(12) United States Patent
Santrock et al.

(10) Patent No.: US 9,622,805 B2
(45) Date of Patent: Apr. 18, 2017

(54) BONE POSITIONING AND PREPARING GUIDE SYSTEMS AND METHODS

(71) Applicant: Treace Medical Concepts, Inc., Ponte Vedra Beach, FL (US)

(72) Inventors: Robert D. Santrock, Morgantown, WV (US); Paul Dayton, Fort Dodge, IA (US); Daniel J. Hatch, Greeley, CO (US); W. Bret Smith, Lexington, SC (US); F. Barry Bays, Collierville, TN (US); Carlos Eduardo Gil, Jacksonville, FL (US); Sean F. Scanlan, Ponte Vedra Beach, FL (US); Joe William Ferguson, Ponte Vedra Beach, FL (US); John T. Treace, Ponte Vedra Beach, FL (US)

(73) Assignee: Treace Medical Concepts, Inc., Ponte Vedra Beach, FL (US)

( * ) Notice: Subject to any disclaimer, the term of this patent is extended or adjusted under 35 U.S.C. 154(b) by 0 days.

(21) Appl. No.: 14/981,335

(22) Filed: Dec. 28, 2015

(65) Prior Publication Data

US 2017/0042598 A1 Feb. 16, 2017

Related U.S. Application Data

(60) Provisional application No. 62/205,338, filed on Aug. 14, 2015.

(51) Int. Cl.
*A61B 17/88* (2006.01)
*A61B 17/80* (2006.01)
*A61B 17/68* (2006.01)

(52) U.S. Cl.
CPC ...... *A61B 17/8866* (2013.01); *A61B 17/8061* (2013.01); *A61B 2017/681* (2013.01)

(58) Field of Classification Search
CPC ......... A61B 17/88; A61B 17/66; A61B 17/80; A61B 17/8061
USPC ........................................................ 606/105
See application file for complete search history.

(56) References Cited

U.S. PATENT DOCUMENTS

| | | | |
|---|---|---|---|
| 4,159,716 | A | 7/1979 | Borchers |
| 4,187,840 | A | 2/1980 | Watanabe |
| 4,338,927 | A | 7/1982 | Volkov et al. |
| 4,627,425 | A | 12/1986 | Reese |

(Continued)

FOREIGN PATENT DOCUMENTS

| | | |
|---|---|---|
| AU | 2009227957 B2 | 7/2014 |
| CA | 2491824 A1 | 9/2005 |

(Continued)

OTHER PUBLICATIONS

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

(Continued)

*Primary Examiner* — Christopher Beccia
(74) *Attorney, Agent, or Firm* — Fredrikson & Byron, P.A.

(57) ABSTRACT

Methods for temporarily fixing an orientation of a bone or bones. Methods of correcting a bunion deformity. Bone positioning devices. Methods of using a bone positioning device. Bone preparation guides. Methods of using a bone preparation guide.

14 Claims, 42 Drawing Sheets

(56) References Cited

U.S. PATENT DOCUMENTS

| | | |
|---|---|---|
| 4,757,810 A | 7/1988 | Reese |
| 4,952,214 A | 8/1990 | Comparetto |
| 4,978,347 A | 12/1990 | Ilizarov |
| 5,021,056 A | 6/1991 | Hofmann et al. |
| 5,112,334 A | 5/1992 | Alchermes et al. |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,413,579 A | 5/1995 | Du Toit |
| 5,449,360 A | 9/1995 | Schreiber |
| H1706 H | 1/1998 | Mason |
| 5,810,822 A | 9/1998 | Mortier |
| 5,893,553 A | 4/1999 | Pinkous |
| 5,935,128 A | 8/1999 | Carter et al. |
| 6,030,391 A | 2/2000 | Brainard et al. |
| 6,719,773 B1 | 4/2004 | Boucher et al. |
| 6,743,233 B1 | 6/2004 | Baldwin et al. |
| 7,033,361 B2 | 4/2006 | Collazo |
| 7,182,766 B1 | 2/2007 | Mogul |
| 7,241,298 B2 | 7/2007 | Nemec et al. |
| 7,377,924 B2 | 5/2008 | Raistrick et al. |
| 7,465,303 B2 | 12/2008 | Riccione et al. |
| 7,641,660 B2 | 1/2010 | Lakin et al. |
| D610,257 S | 2/2010 | Horton |
| 7,686,811 B2 | 3/2010 | Byrd et al. |
| D629,900 S | 12/2010 | Fisher |
| 7,972,338 B2 | 7/2011 | O'Brien |
| D646,389 S | 10/2011 | Claypool et al. |
| 8,057,478 B2 | 11/2011 | Kuczynski et al. |
| D651,315 S | 12/2011 | Bertoni et al. |
| D651,316 S | 12/2011 | May et al. |
| 8,080,010 B2 | 12/2011 | Schulz et al. |
| 8,123,753 B2 | 2/2012 | Dubriske |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,663 B2 | 7/2012 | Kay et al. |
| 8,246,561 B1 | 8/2012 | Agee et al. |
| D666,721 S | 9/2012 | Wright et al. |
| 8,262,664 B2 | 9/2012 | Justin et al. |
| 8,282,644 B2 | 10/2012 | Edwards |
| 8,282,645 B2 | 10/2012 | Lawrence et al. |
| 8,292,966 B2 | 10/2012 | Morton |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Büscher |
| D679,395 S | 4/2013 | Wright et al. |
| 8,435,246 B2 | 5/2013 | Fisher et al. |
| 8,475,462 B2 | 7/2013 | Thomas et al. |
| 8,523,870 B2 | 9/2013 | Green, II et al. |
| D694,884 S | 12/2013 | Mooradian et al. |
| D695,402 S | 12/2013 | Dacosta et al. |
| 8,652,142 B2 | 2/2014 | Geissler |
| D701,303 S | 3/2014 | Cook |
| 8,672,945 B2 | 3/2014 | LaVallee et al. |
| 8,696,716 B2 | 4/2014 | Kartalian et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,763 B2 | 7/2014 | Wong et al. |
| 8,771,279 B2 | 7/2014 | Philippon et al. |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| 2002/0198531 A1 | 12/2002 | Millard et al. |
| 2004/0039394 A1 | 2/2004 | Conti et al. |
| 2004/0097946 A1 | 5/2004 | Dietzel et al. |
| 2005/0004676 A1 | 1/2005 | Schon et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0273112 A1 | 12/2005 | McNamara |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0091197 A1 | 4/2008 | Coughlin |
| 2008/0140081 A1 | 6/2008 | Heavener |
| 2008/0208252 A1 | 8/2008 | Holmes |
| 2008/0262500 A1 | 10/2008 | Callazo |
| 2008/0269908 A1 | 10/2008 | Warburton |
| 2009/0036893 A1 | 2/2009 | Kartalian et al. |
| 2009/0093849 A1 | 4/2009 | Grabowski |
| 2009/0105767 A1 | 4/2009 | Reiley |
| 2009/0198244 A1 | 8/2009 | Leibel |
| 2009/0222047 A1 | 9/2009 | Graham |
| 2009/0254092 A1 | 10/2009 | Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0256687 A1 | 10/2010 | Neufeld et al. |
| 2010/0324556 A1 | 12/2010 | Tyber et al. |
| 2011/0093084 A1 | 4/2011 | Morton |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1* | 1/2012 | Robinson ............... A61B 17/68 606/328 |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130383 A1 | 5/2012 | Budoff |
| 2012/0184961 A1 | 7/2012 | Johannaber |
| 2012/0239045 A1 | 9/2012 | Li |
| 2012/0253350 A1 | 10/2012 | Anthony et al. |
| 2012/0265301 A1 | 10/2012 | Demers et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1* | 7/2013 | Lewis ............... A61B 17/8061 606/281 |
| 2013/0184714 A1 | 7/2013 | Kaneyama et al. |
| 2013/0190765 A1 | 7/2013 | Harris et al. |

(56) References Cited

U.S. PATENT DOCUMENTS

| | | |
|---|---|---|
| 2013/0190766 A1 | 7/2013 | Harris et al. |
| 2013/0204259 A1 | 8/2013 | Zajac |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325076 A1 | 12/2013 | Plamer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter et al. |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0194884 A1 | 7/2014 | Martin et al. |
| 2014/0207144 A1 | 7/2014 | Lee et al. |
| 2014/0249537 A1 | 9/2014 | Wong et al. |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0296995 A1 | 10/2014 | Reiley et al. |
| 2014/0336658 A1 | 11/2014 | Luna et al. |
| 2015/0032168 A1 | 1/2015 | Orsak et al. |
| 2015/0045839 A1 | 2/2015 | Dacosta et al. |
| 2015/0051650 A1 | 2/2015 | Verstreken et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| EP | 0685206 B1 | 9/2000 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| FR | 2362616 A1 | 3/1978 |
| FR | 2764183 B1 | 11/1999 |
| FR | 3030221 A1 | 6/2016 |
| GB | 2154143 A | 9/1985 |
| GB | 2154144 A | 9/1985 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 2008051064 A1 | 5/2008 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015105880 A1 | 7/2015 |
| WO | 2015127515 A2 | 9/2015 |

OTHER PUBLICATIONS

Anderson et al., "Uncemented STAR Total Ankle Prostheses," The Journal of Bone and Joint Surgery, vol. 86(1, Suppl 2), Sep. 2004, pp. 103-111, (Abstract Only).

Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).

(56) References Cited

OTHER PUBLICATIONS

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"HAT-TRICK Lesser Toe Repair System," Smith & Nephew, Brochure, Aug. 2014, 12 pages.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
"Lag Screw Target Bow," Stryker Leibinger GmbH & Co. KG, Germany 2004, 8 pages.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Rx-Fix Mini Rail External Fixator, Wright Medical Technology, Brochure, Aug. 15, 2014, 2 pages.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
TempFix Spanning the Ankle Joint Half Pin and Transfixing Pin Techniques, Biomet Orthopedics, Surgical Technique, 2012, 16 pages.
Weber et al., "A Simple System For Navigation Of Bone Alignment Osteotomies Of The Tibia," International Congress Series, vol. 1268, Jan. 2004, pp. 608-613, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Talbot et al.,"Assessing Sesamoid Subluxation: How Good is the AP Radiograph?," Foot and Ankle International, vol. 19, No. 8, Aug. 1998, pp. 547-554.
Yasuda et al., "Proximal Suination Osteotomy of the First Metatarsal for Hallux Valgus," Foot and Ankle International, vol. 36, No. 6, Jun. 2015, pp. 696-704.
International Patent Application No. PCT/US2016/046892, International Search Report and Written Opinion mailed Dec. 28, 2016, 18 pages.

\* cited by examiner

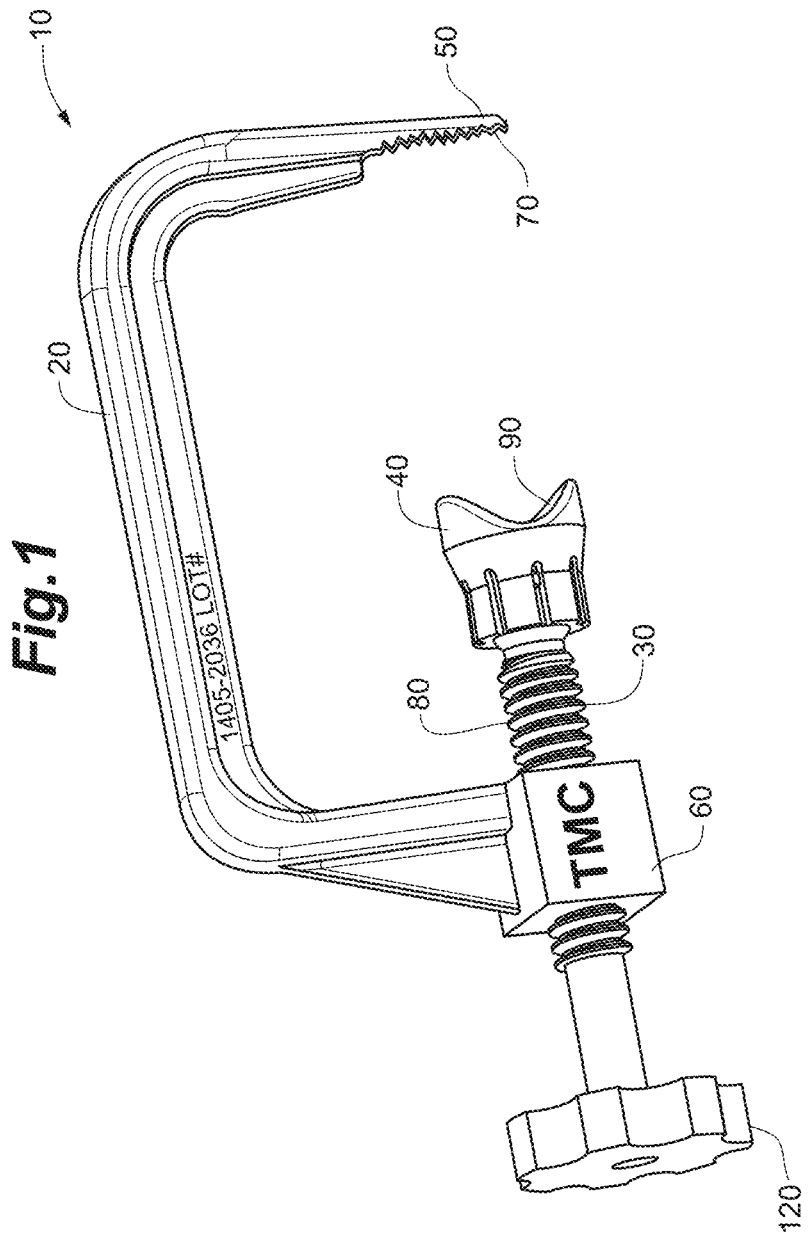

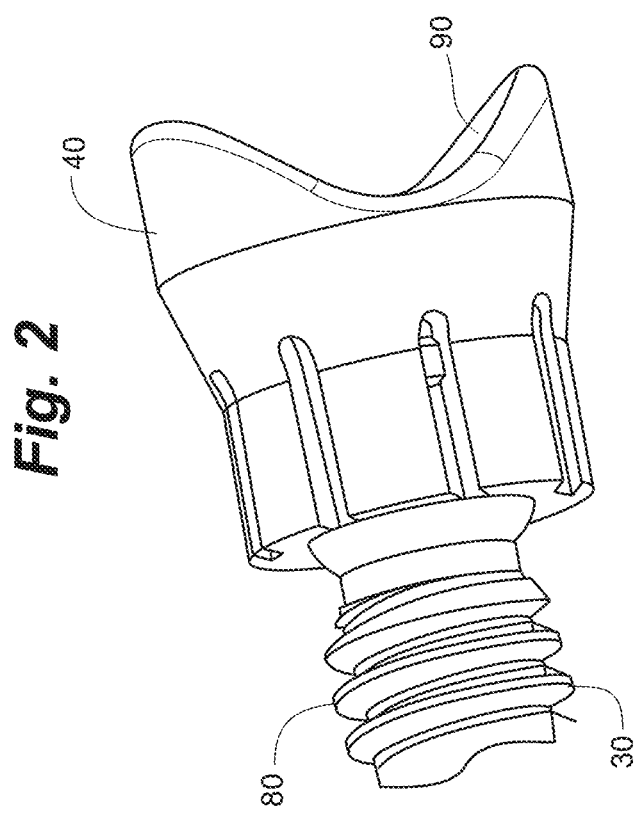

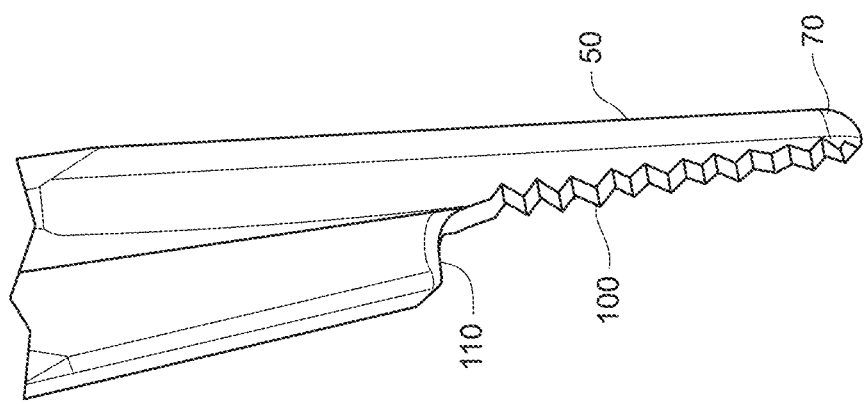

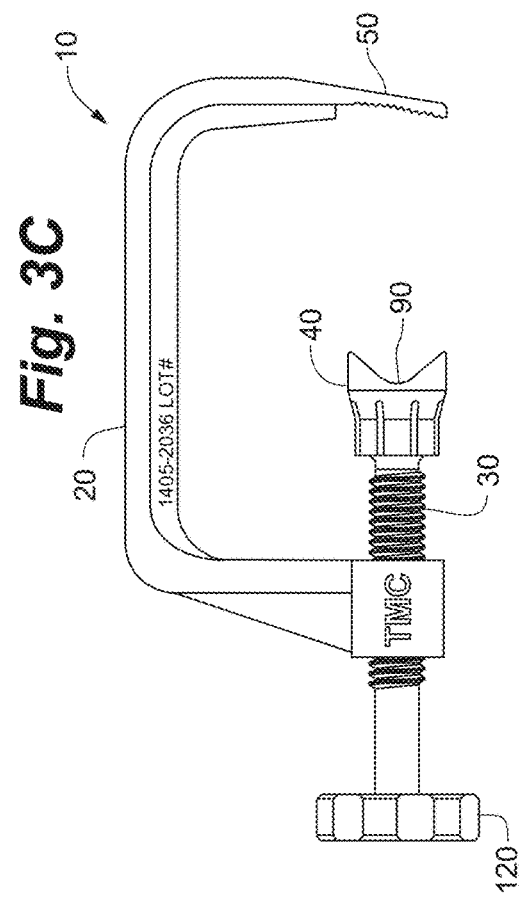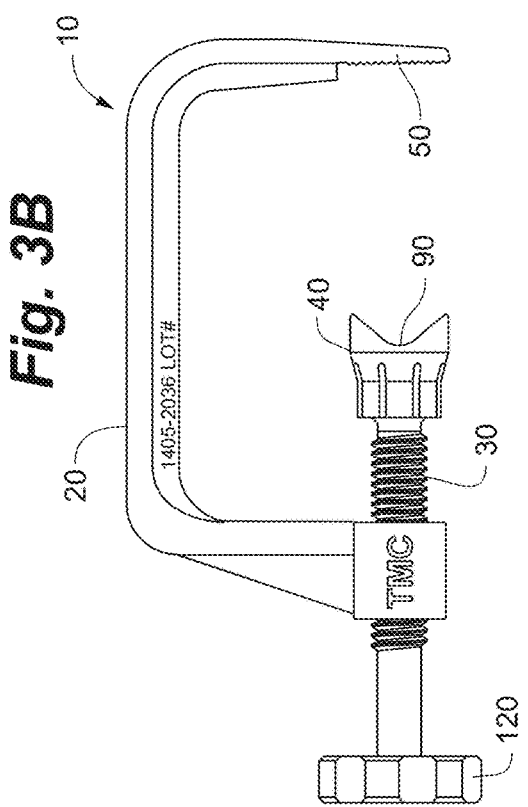

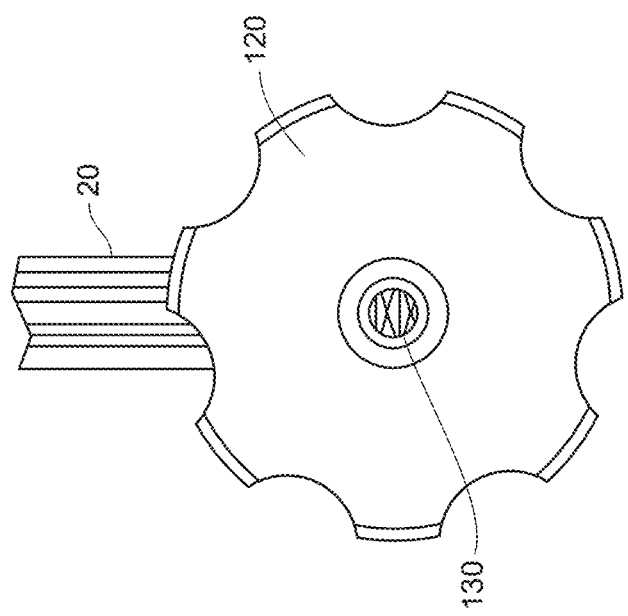

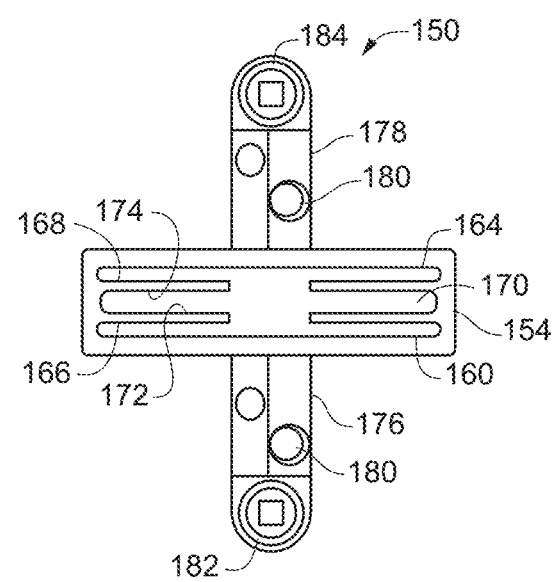

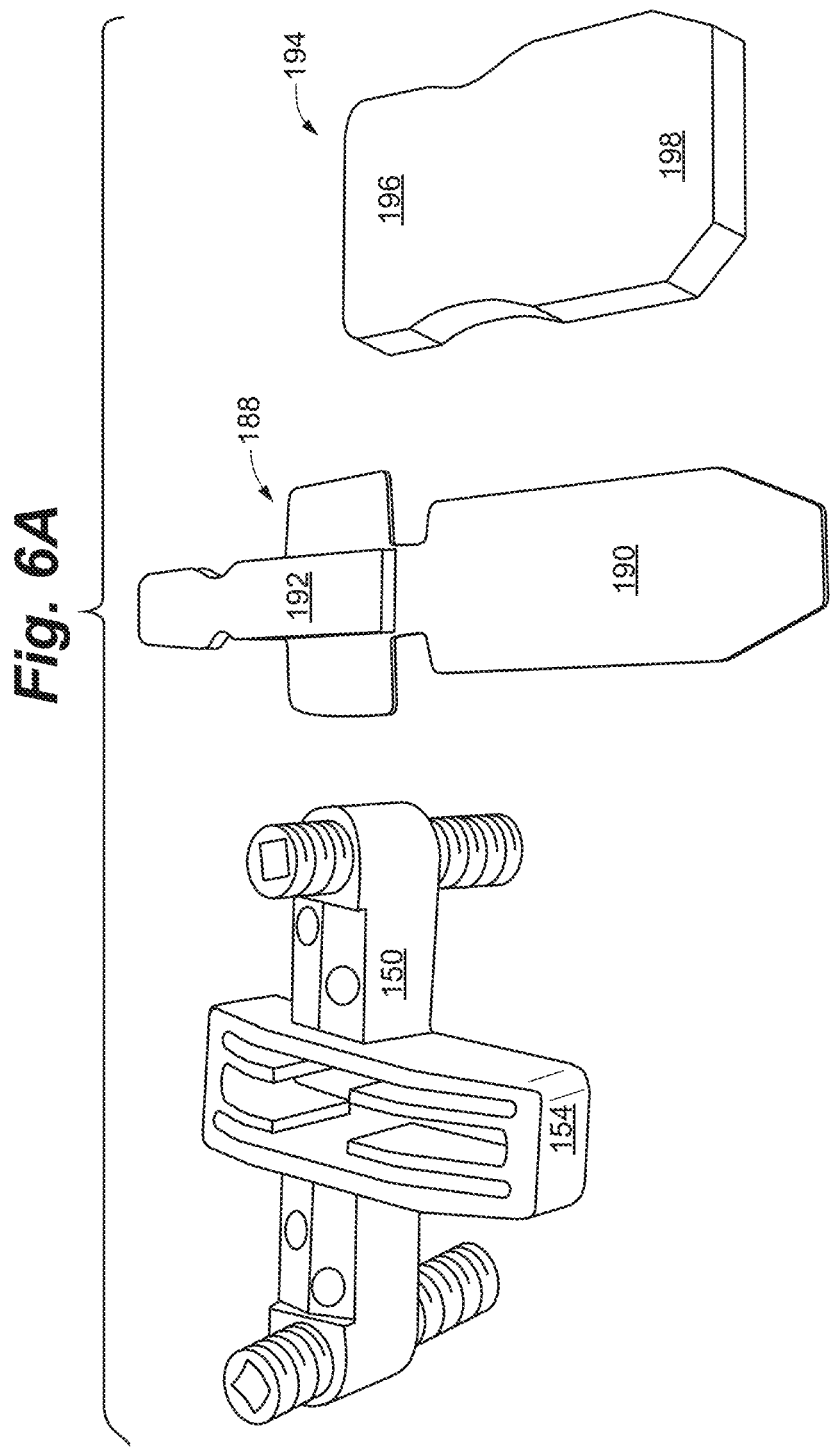

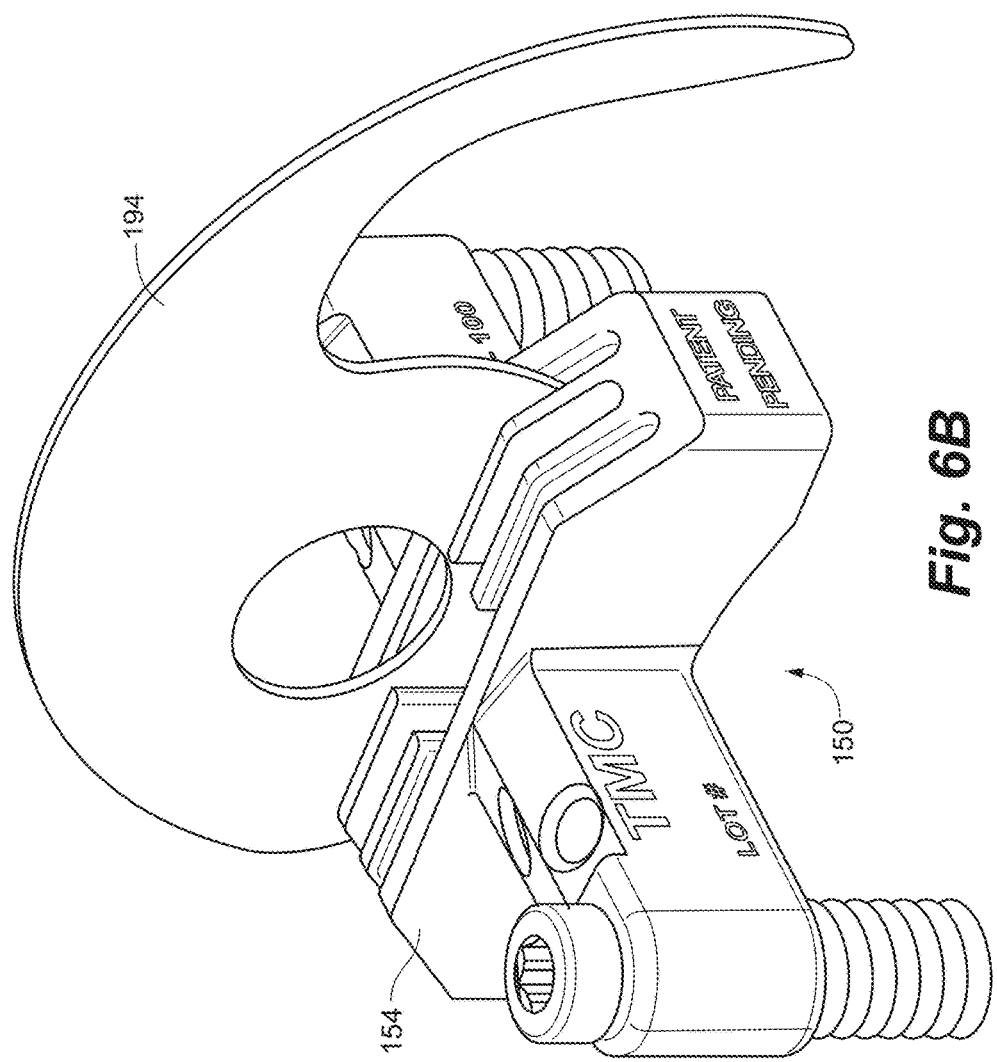

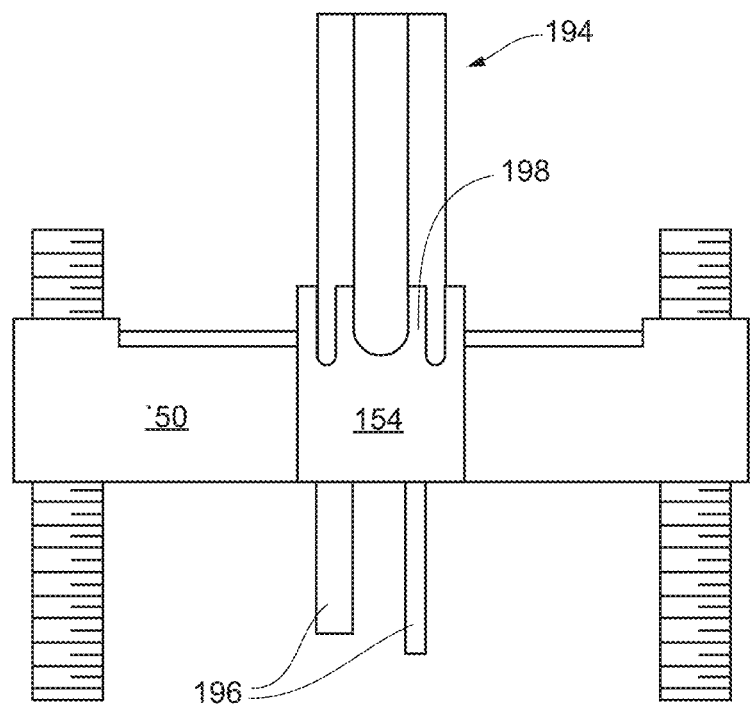

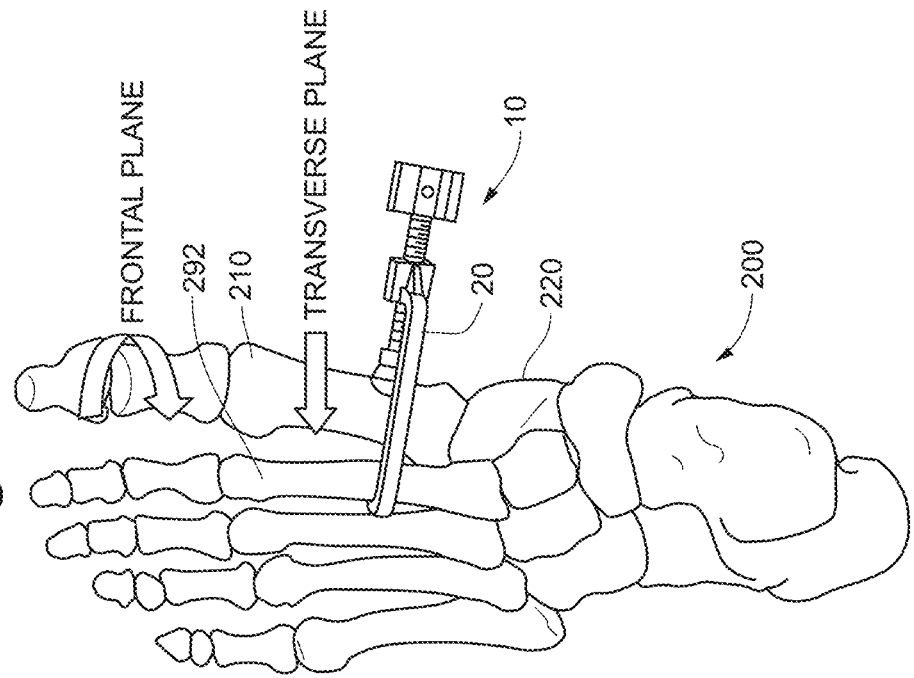
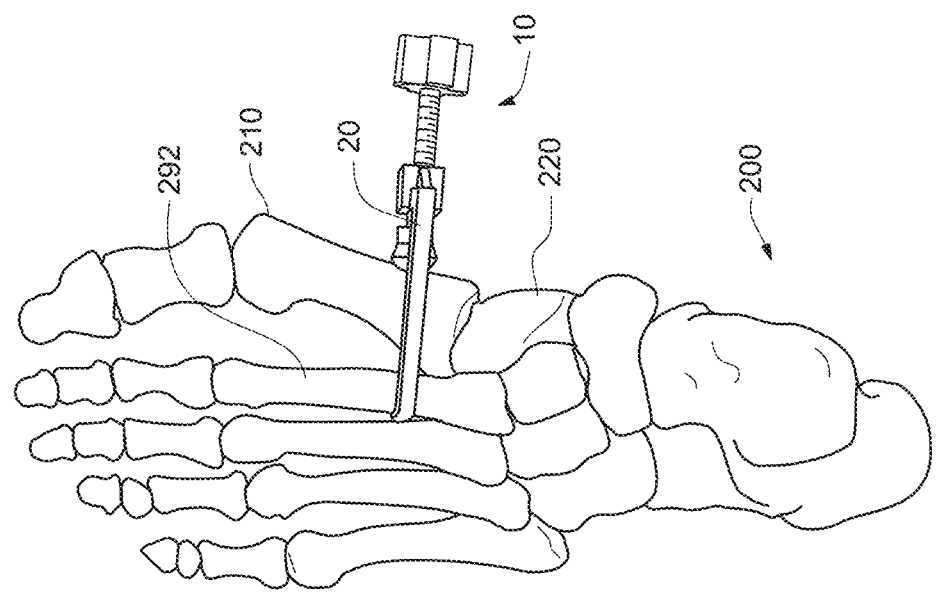

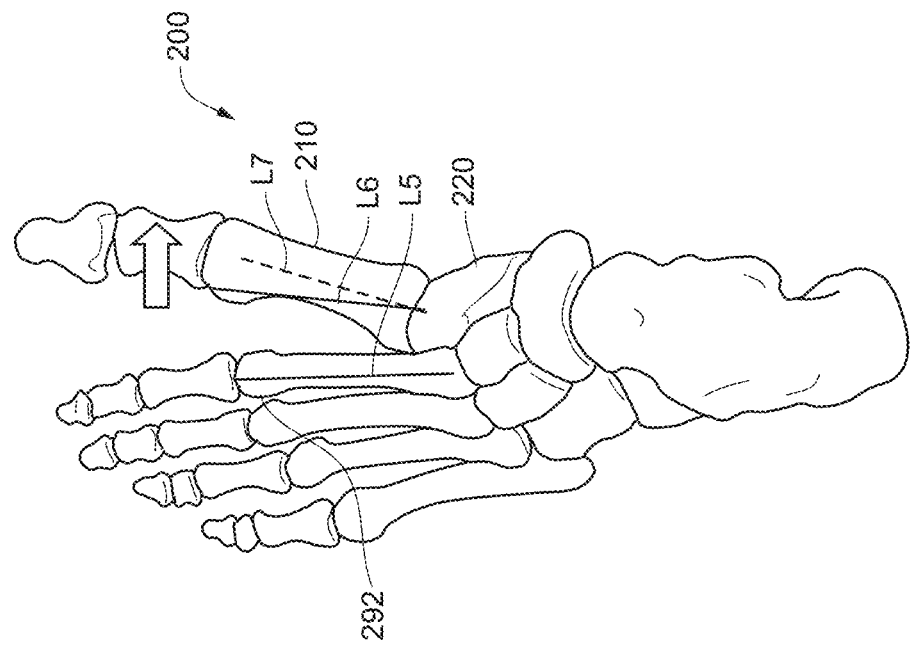
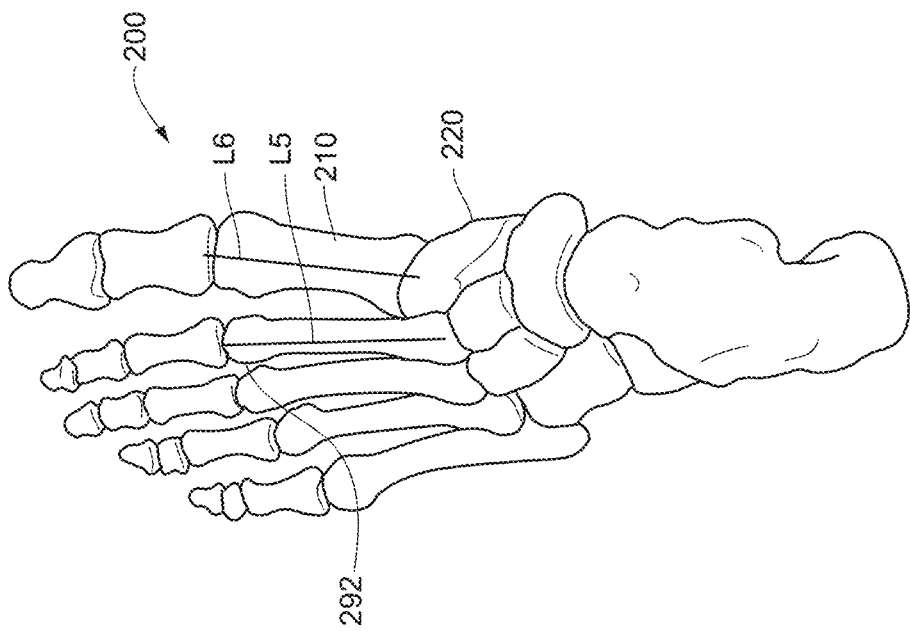

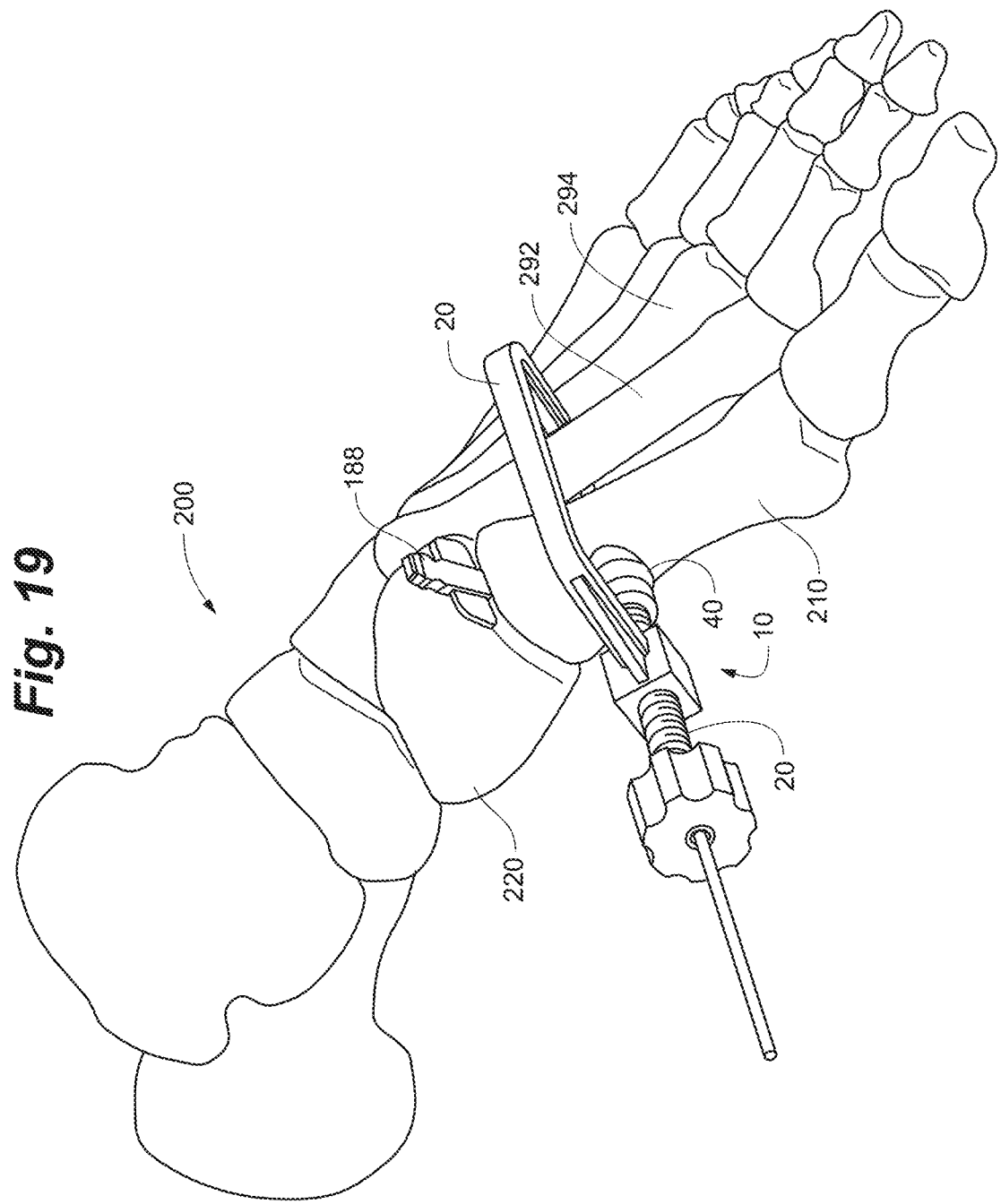

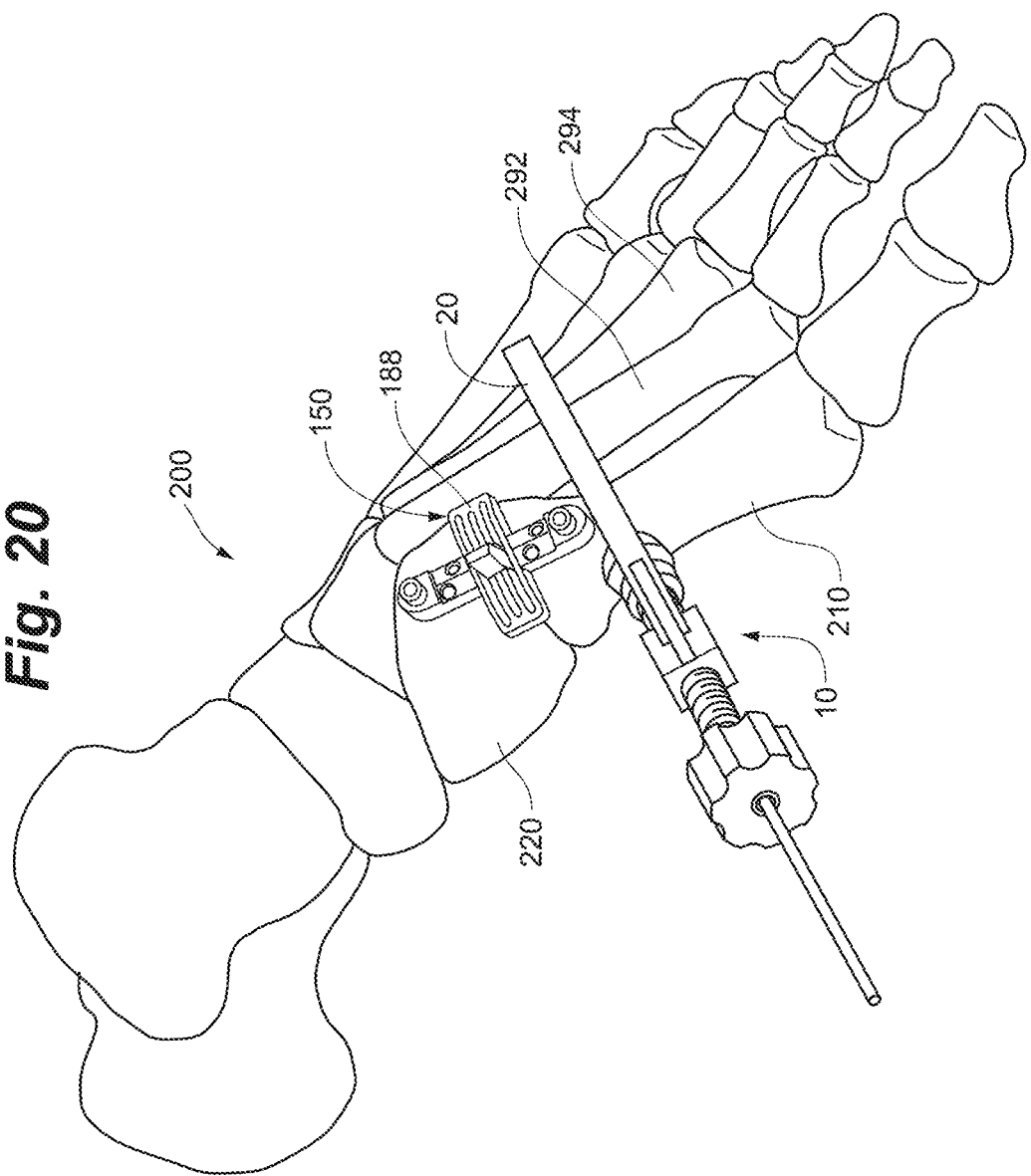

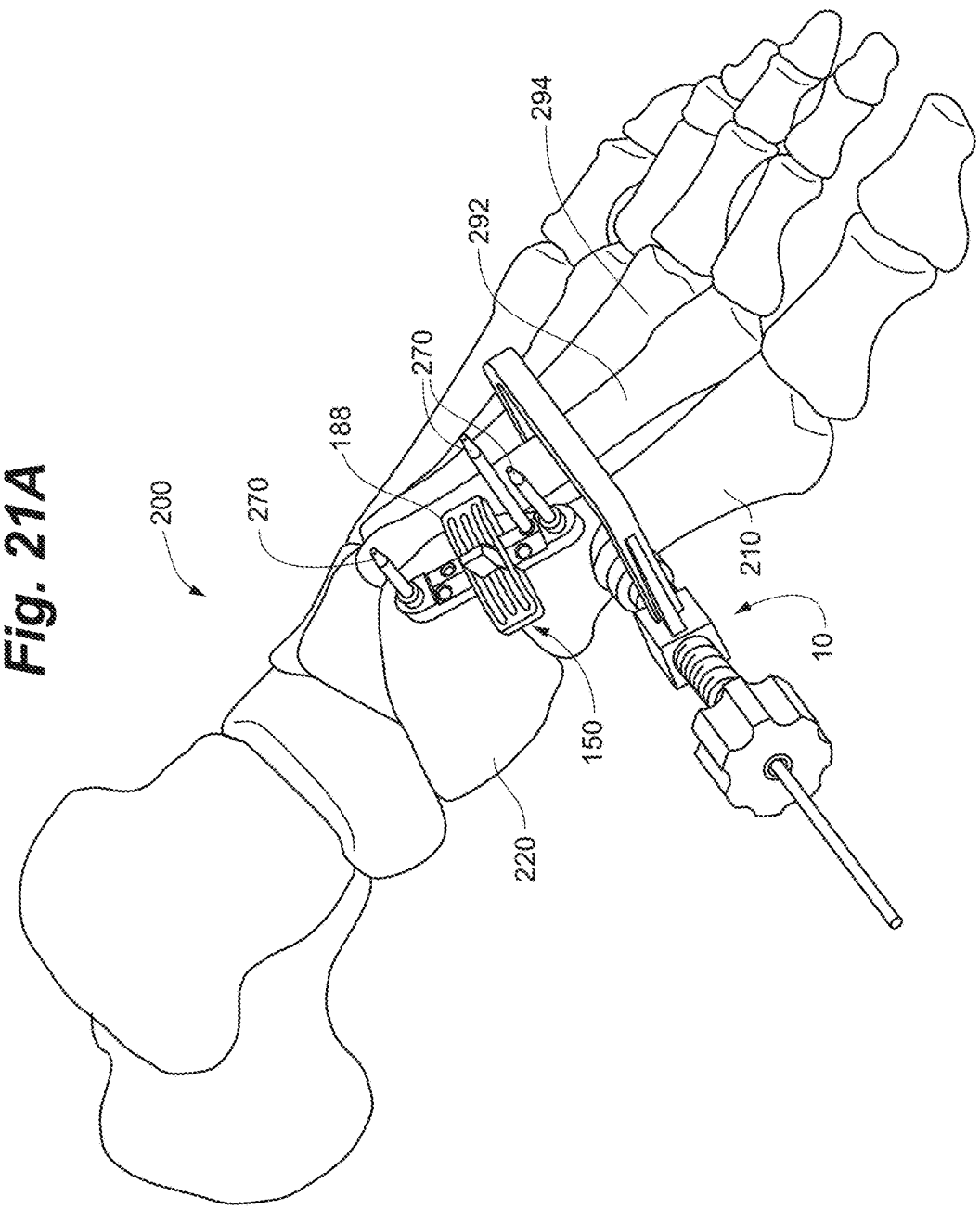

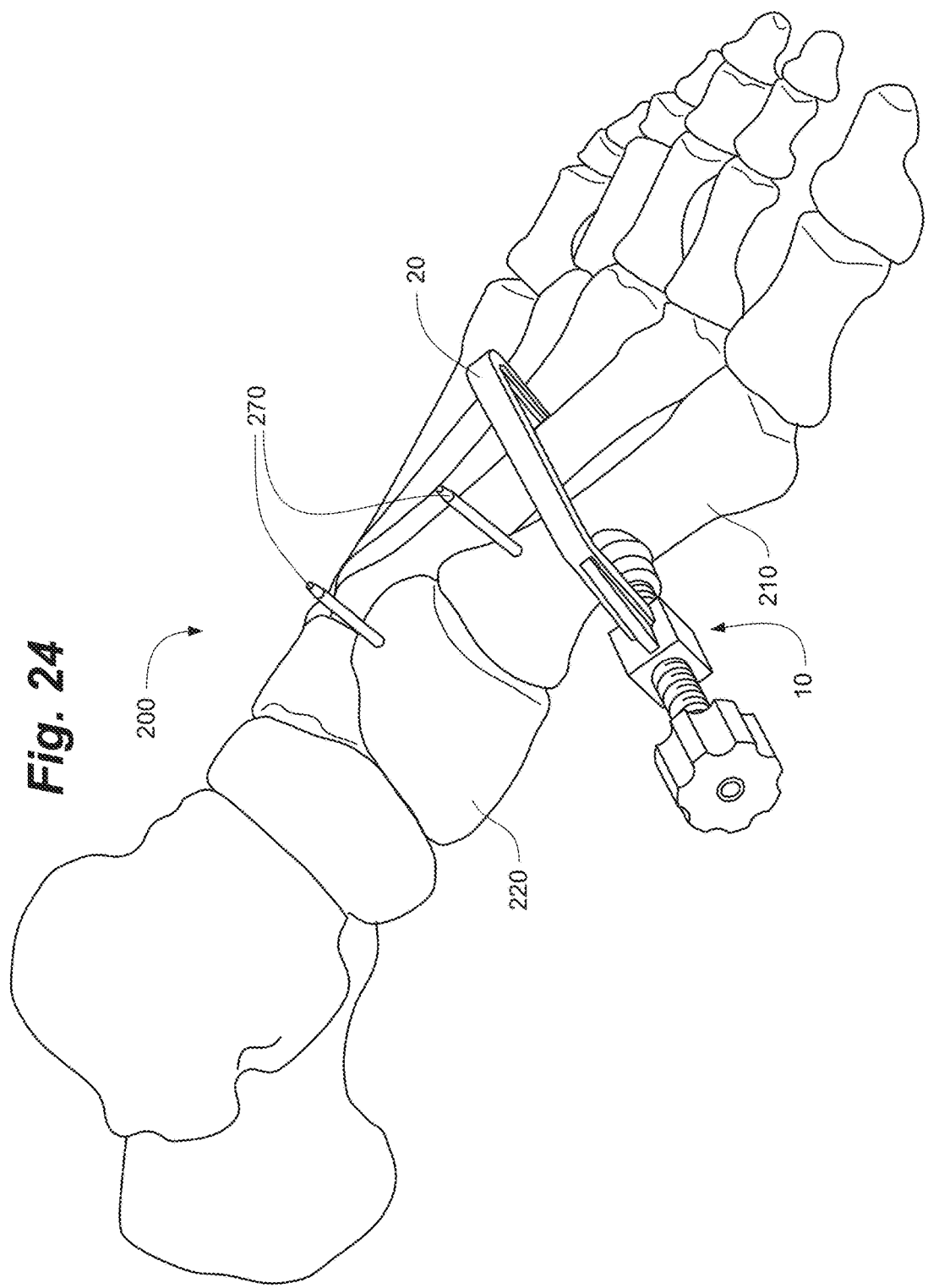

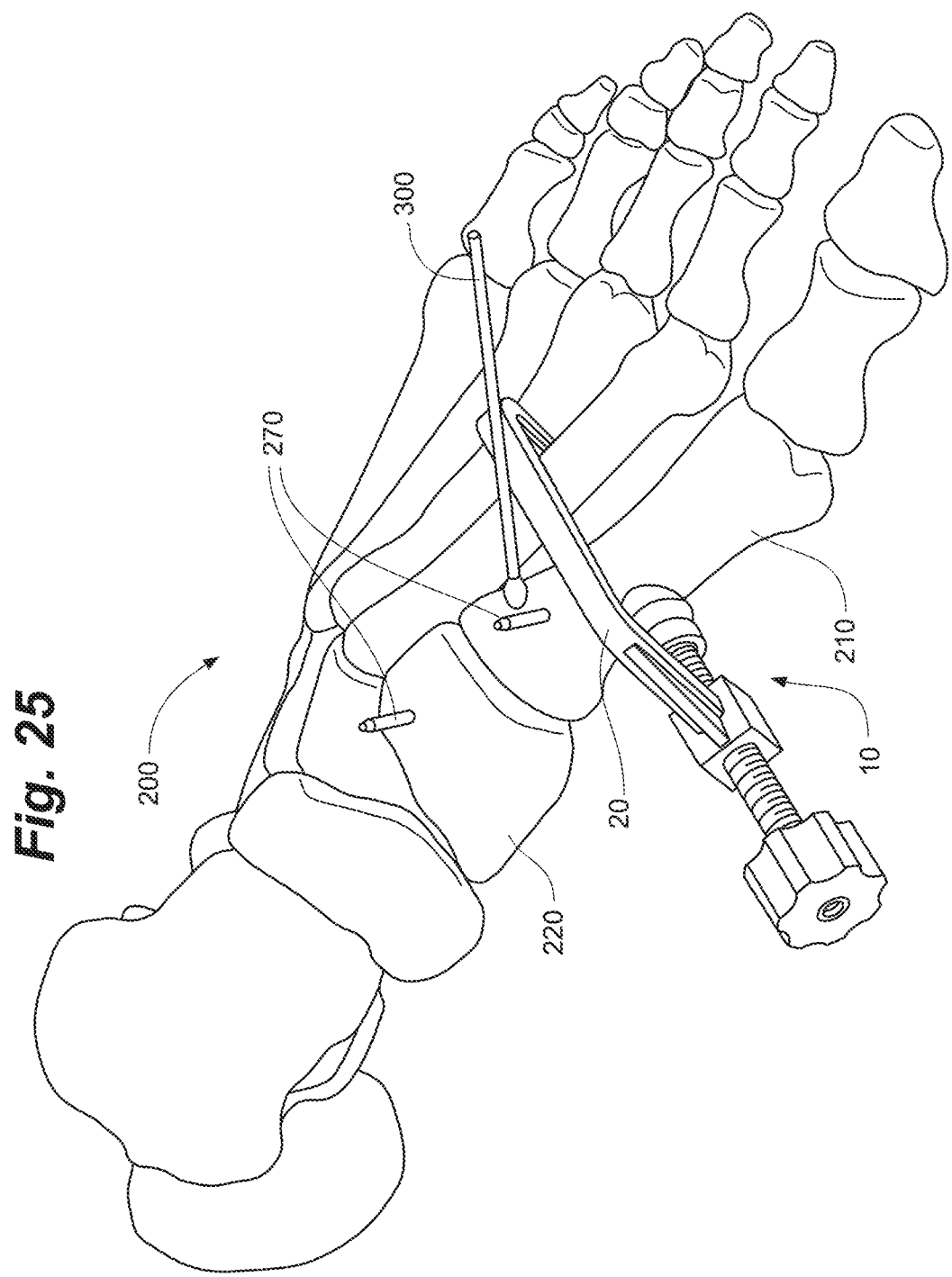

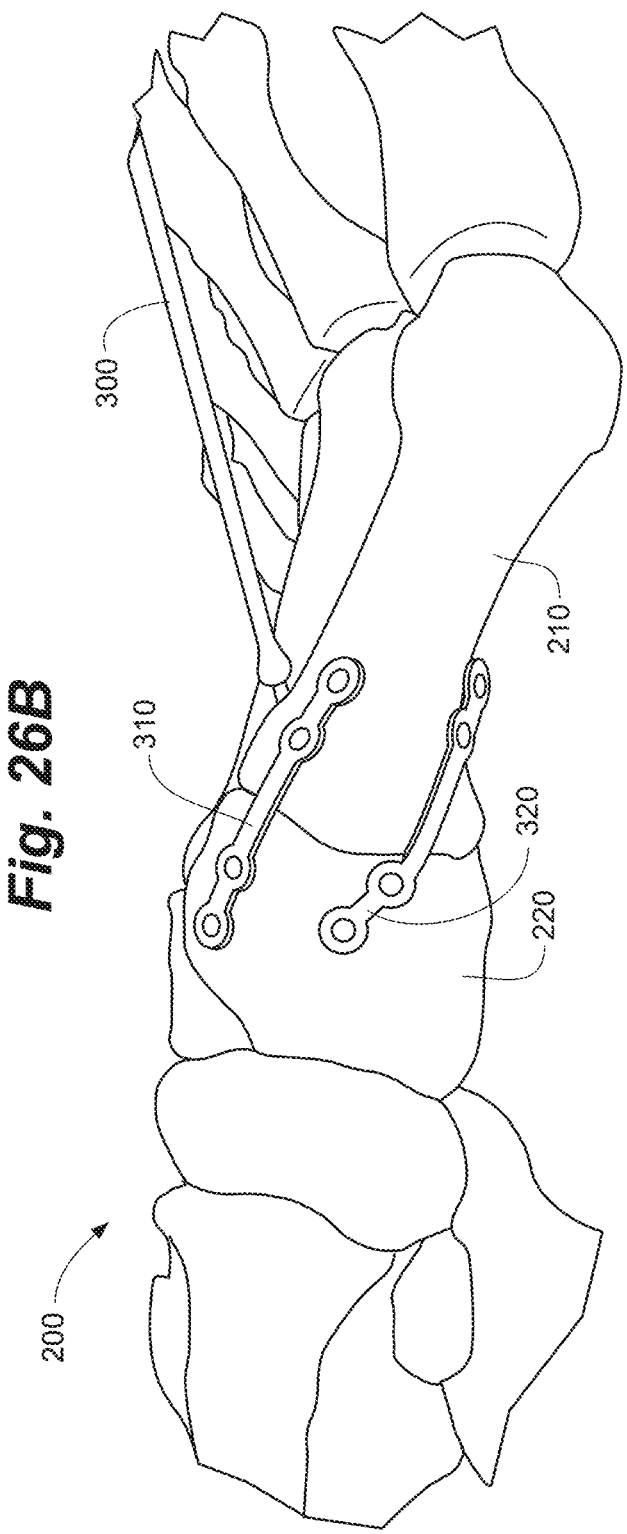

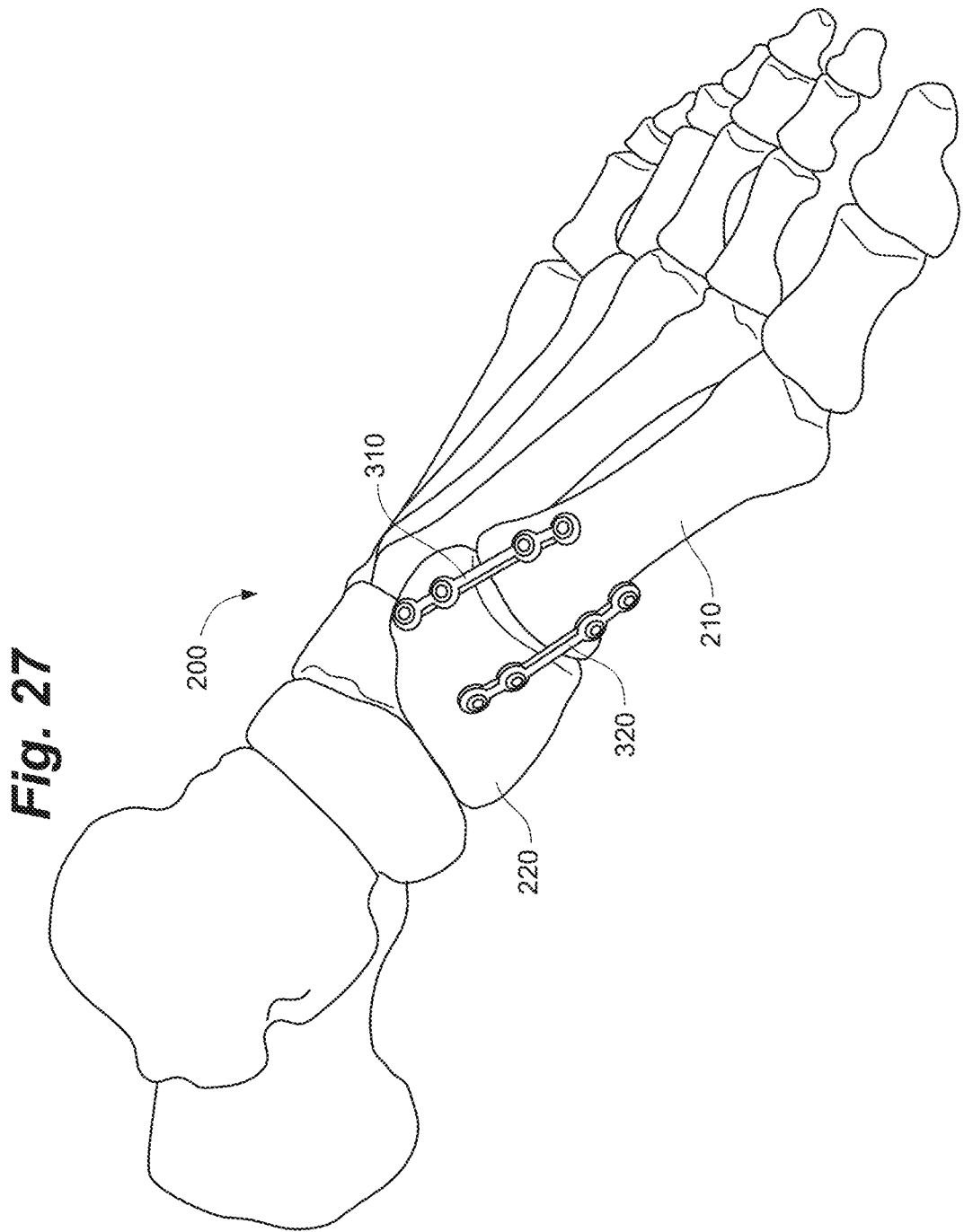

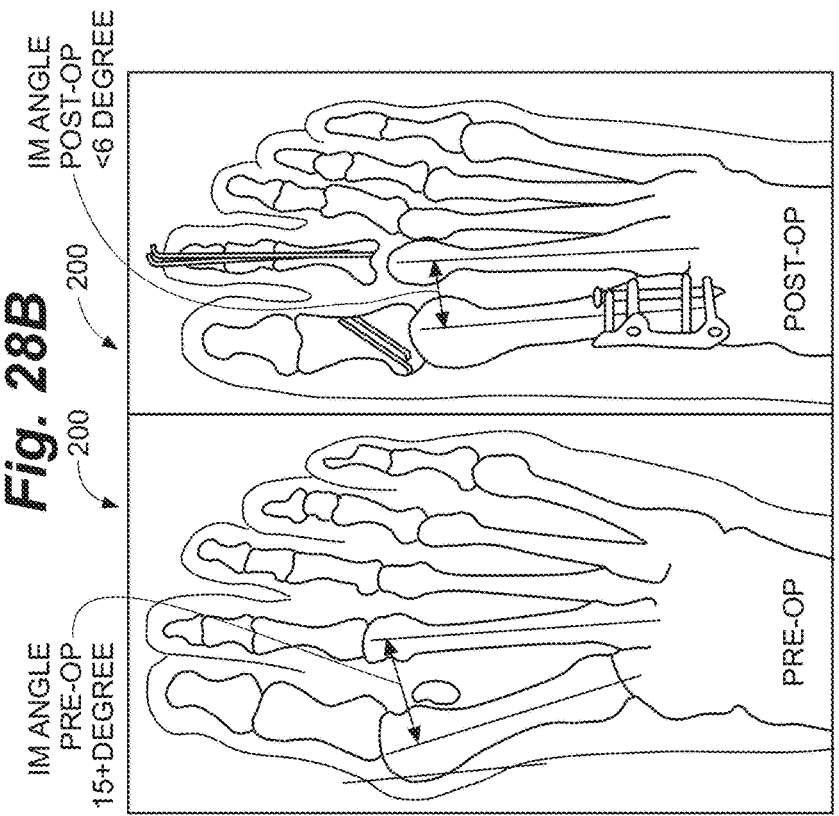
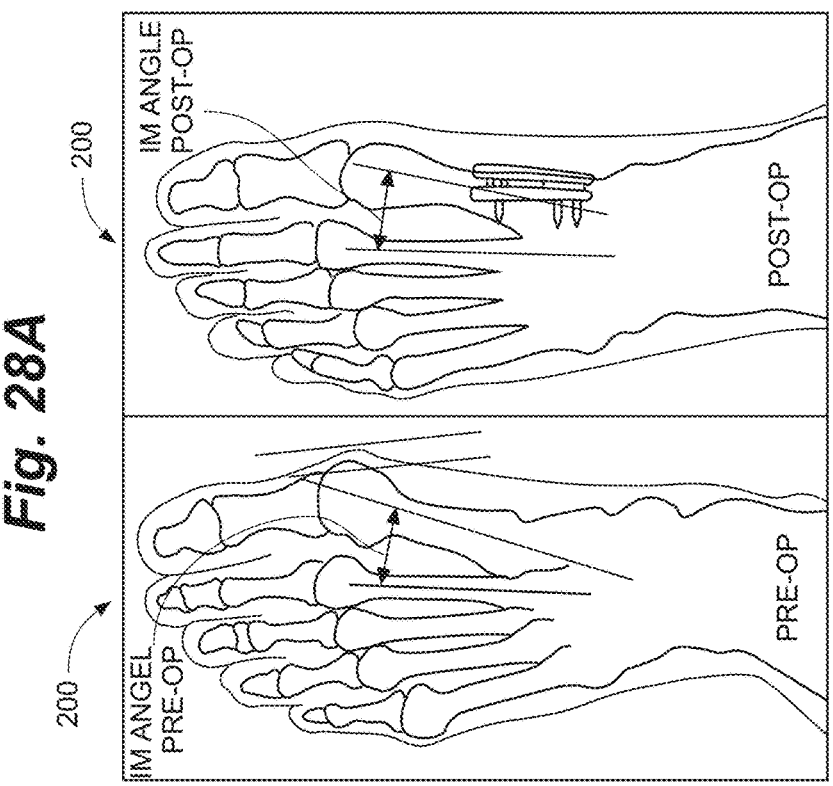
Fig. 28A
Fig. 28B

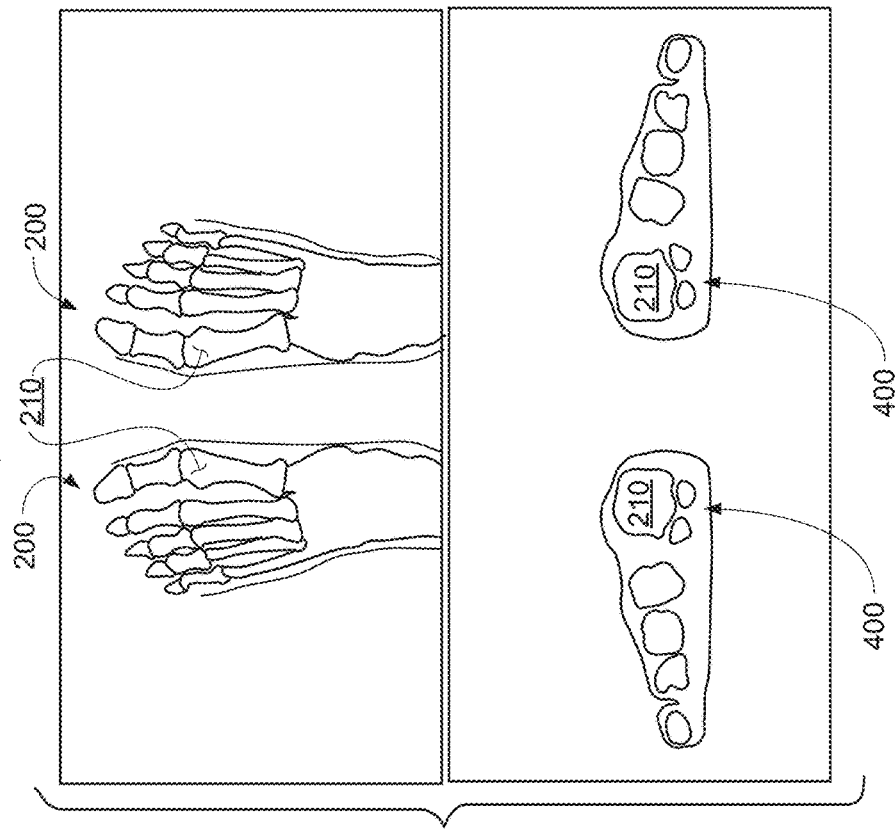
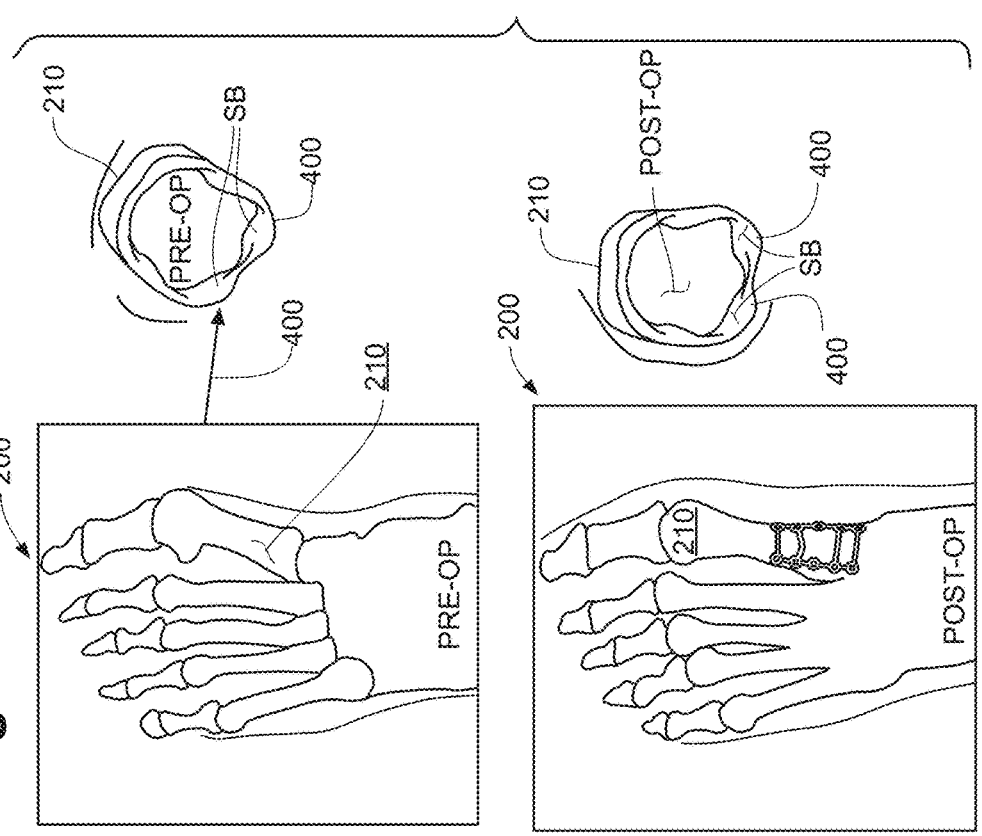
Fig. 29B
Fig. 29A

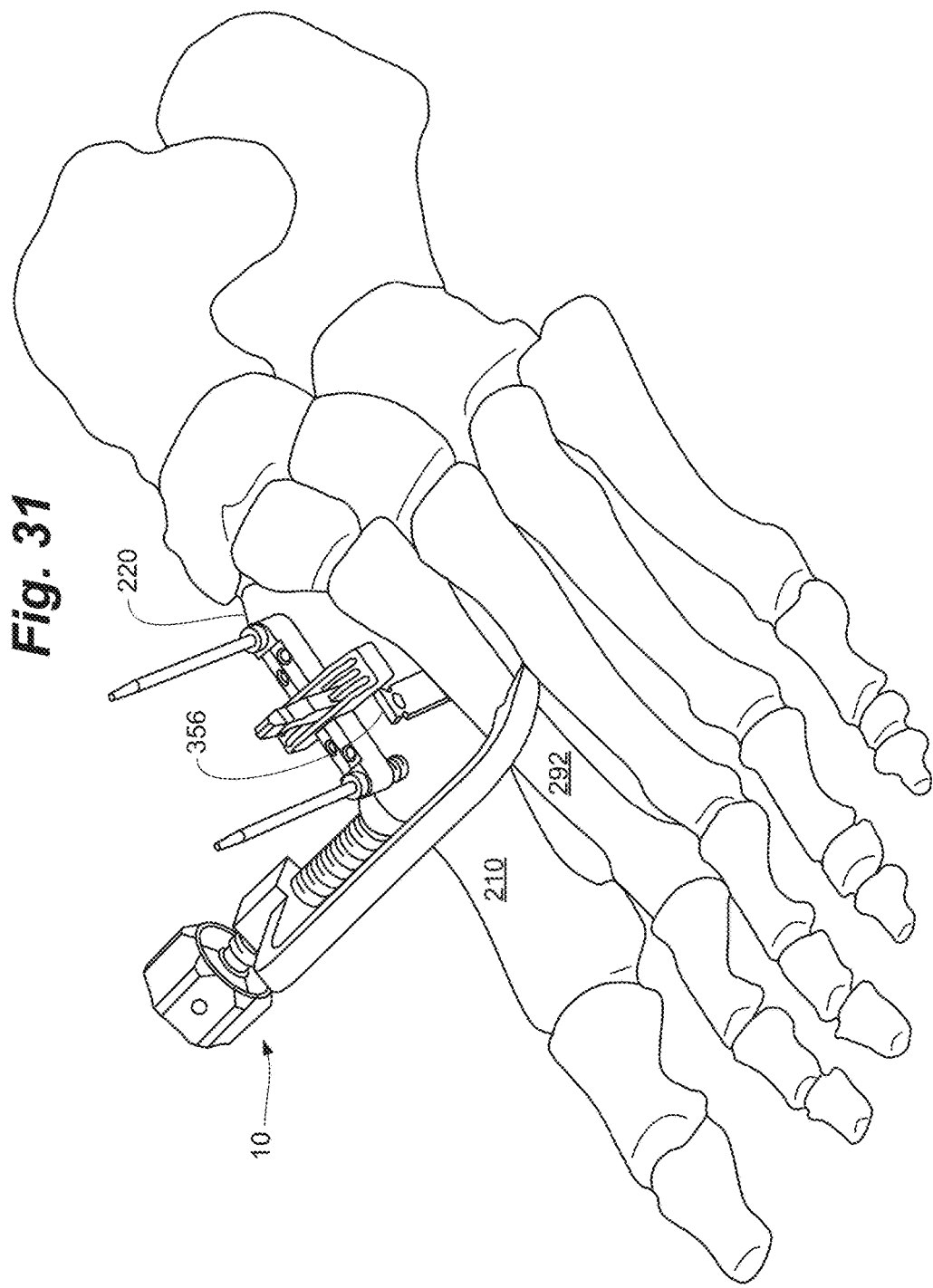

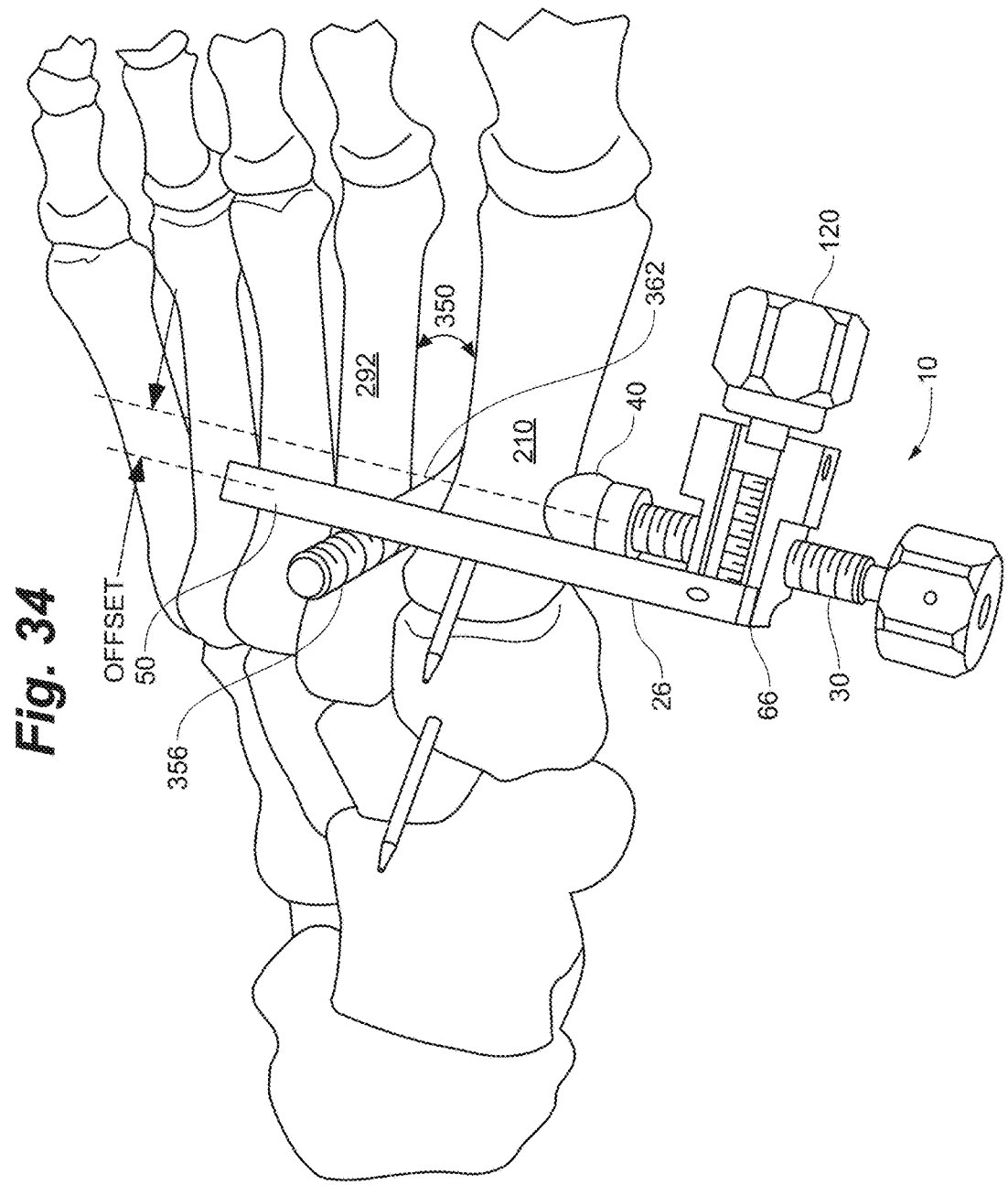

BONE POSITIONING AND PREPARING GUIDE SYSTEMS AND METHODS

RELATED APPLICATION

This application claims the benefit of U.S. Provisional Application Ser. No. 62/205,338, filed Aug. 14, 2015, the contents of which are hereby incorporated by reference.

TECHNICAL FIELD

This disclosure relates generally to devices and methods for positioning and/or preparing bones.

BACKGROUND

Bones, such as the bones of a foot, may be anatomically misaligned. In certain circumstances, surgical intervention is required to correctly align the bones to reduce patient discomfort and improve patient quality of life.

SUMMARY

Embodiments of the present invention include methods for temporarily fixing an orientation of a bone or bones. In general, the method of positioning a bone includes the steps of moving a bone from an anatomically misaligned position to an anatomically aligned position with respect to another bone and preparing an end of the bone and a facing end of another bone. In some embodiments, at least one bone end is prepared after the bone is moved into the aligned position. In some embodiments, the bone is anatomically aligned in more than one plane such that the bone both translates and rotates in response to a moving force.

One embodiment includes a method of correcting a bunion deformity. The method has the steps of moving a first metatarsal from an anatomically misaligned position with respect to a second metatarsal to an anatomically aligned position with respect to the second metatarsal by applying a force to the first metatarsal, the force moving the first metatarsal to correct an alignment in more than one plane. The method can also include preparing an end of the first metatarsal and preparing an opposing end of a medial cuneiform for fusion. Embodiments of the invention also include a bone positioning device and a bone preparation guide, and methods of using such guides.

BRIEF DESCRIPTION OF THE DRAWINGS

The following drawings are illustrative of particular embodiments of the present invention and, therefore, in no way limit the scope of the invention. The drawings are not necessarily to scale (unless otherwise stated) and are intended for use in conjunction with the explanations in the following detailed description. Embodiments of the invention will hereinafter be described with respect to the appended drawings, wherein like numerals denote like elements.

FIG. 1 is a side perspective view of a bone positioning guide in accordance with an embodiment of the invention.

FIG. 2 is a side perspective view of a bone engagement member of a bone positioning guide in accordance with an embodiment of the invention.

FIG. 3A is a side perspective view of a tip of a bone positioning guide in accordance with an embodiment of the invention.

FIG. 3B is a side view of a bone positioning guide with a straight tip in accordance with an embodiment of the invention.

FIG. 3C is a side view of a bone positioning guide with a nonlinear tip in accordance with an embodiment of the invention.

FIG. 4 is an end view of an actuator of a bone positioning guide in accordance with an embodiment of the invention.

FIG. 5 is a top plan view of a bone preparing guide in accordance with an embodiment of the invention.

FIG. 6A is a perspective view of a bone preparing guide, a spacer, and a tissue removing instrument location check member in accordance with an embodiment of the invention.

FIG. 6B is a perspective view of another embodiment of a tissue removing instrument check location member engaged with a bone preparing guide.

FIG. 8 is a perspective view of a bone preparing guide engaged with a tissue removal instrument location check member in accordance with an embodiment of the invention.

FIG. 10A is a top view of a bone positioning guide on a deformed foot in accordance with an embodiment of the invention.

FIG. 10B is a top view of a bone positioning guide on a foot with a corrected alignment in accordance with an embodiment of the invention.

FIG. 13A is a top view of a foot with a normal first metatarsal position.

FIG. 13B is a top view of a foot with an isolated first metatarsal transverse plane bunion deformity.

FIG. 19 is a perspective view of a foot depicting a bone positioning guide on the foot after an alignment of a first metatarsal and an insertion of a spacer into a joint space.

FIG. 20 is a perspective view of a foot depicting a bone positioning guide on the foot after an alignment of a first metatarsal and a positioning of a bone preparation guide.

FIG. 21A is a perspective view of a foot depicting a bone positioning guide on the foot after an alignment of a first metatarsal and a positioning of a bone preparation guide with pins.

FIG. 24 is a perspective view of a foot depicting a bone positioning guide on the foot and pins.

FIG. 25 is a perspective view of a foot depicting a bone positioning guide on the foot and a compression pin.

FIG. 26B is a side perspective view of a foot depicting bone plates across a joint between first and second bones and a compression pin in accordance with an embodiment of the invention.

FIG. 27 is a side perspective view of a foot depicting bone plates across a joint between first and second bones in accordance with an embodiment of the invention.

FIG. 28A and FIG. 28B depict examples of anatomically misaligned metatarsals and metatarsals that have been anatomically aligned using methods and/or instruments in accordance with the invention.

FIG. 29A and FIG. 29B depict examples of anatomically misaligned metatarsals and metatarsals that have been anatomically aligned using methods and/or instruments in accordance with the invention.

FIG. 31 illustrates an example bone positioning operation in which a fulcrum is positioned at an intersection between a first bone and a second bone.

FIG. 34 is a perspective view of another bone positioning guide according to an embodiment of the invention.

DETAILED DESCRIPTION

Figure 7:
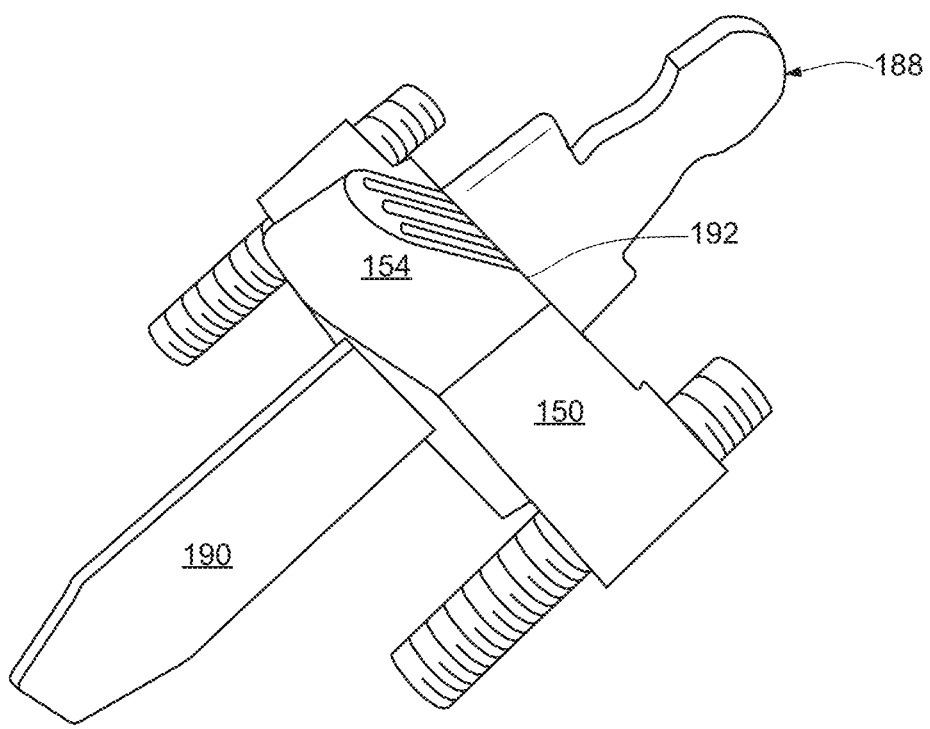
FIG. 7 is a perspective view of a bone preparing guide engaged with a spacer in accordance with an embodiment of the invention.

The following detailed description is exemplary in nature and is not intended to limit the scope, applicability, or configuration of the invention in any way. Rather, the following description provides practical illustrations for implementing exemplary embodiments of the present invention. Examples of constructions, materials, and dimensions are provided for selected elements, and all other elements employ that which is known to those of ordinary skill in the field of the invention. Those skilled in the art will recognize that many of the noted examples have a variety of suitable alternatives.

Embodiments of the invention include a bone positioning guide and method of positioning bones in a medical procedure. In an exemplary application, embodiments of the bone positioning guide can be useful during a surgical procedure, such as a bone alignment, osteotomy, fusion procedure, and/or other procedures where one or more bones are to be prepared (e.g., cartilage or bone removal and/or cut). Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing an embodiment of the bone positioning guide can be performed to correct an alignment between a metatarsal (e.g., a first metatarsal) and a second metatarsal and/or a cuneiform (e.g., a medial, or first, cuneiform), such as in a bunion correction surgery. An example of such a procedure is a Lapidus procedure (also known as a first tarsal-metatarsal fusion). In another example, the procedure can be performed by modifying an alignment of a metatarsal (e.g., a first metatarsal). An example of such a procedure is a basilar metatarsal osteotomy procedure.

FIG. 1 shows a side perspective view of a bone positioning guide 10 in accordance with an embodiment of the invention. The bone positioning guide 10 can be useful for positioning a bone (e.g., orientating and/or translating) during a medical procedure. In some embodiments, the bone positioning guide includes a bone engagement member, a tip, a mechanism to urge the bone engagement member and the tip towards each other (e.g. moving the bone engagement member towards the tip, moving the tip towards the bone engagement member, or moving both simultaneously), and an actuator to actuate the mechanism. When the mechanism is actuated it causes a first bone engaged with the bone engagement member to move to correct an alignment in more than one plane with respect to a second bone in contact with the tip. In some embodiments, the correction in more than one plane includes a correction about an axis in a frontal plane.

In the embodiment of FIG. 1, bone positioning guide 10 includes a main body member 20 and a shaft 30, and the bone engagement member 40 is connected to the shaft and the tip 50 is connected to the main body member. In general, the main body member 20 can be sized and shaped to clear anatomy or other instrumentation (e.g., pins and guides) while positioned on a patient. In the embodiment of FIG. 1, the main body member 20 includes a generally C-shaped configuration with a first end 60 and a second end 70. In some embodiments, the main body is sized and configured to engage bones of a human foot. In addition, although bone positioning guide 10 is illustrated as being formed of two components, main body member 20 and shaft 30, the guide can be fabricated from more components (e.g., 3, 4, or more) that are joined together to form the guide.

A shaft 30 can be movably connected to the main body member 20 proximate its first end 60. In some embodiments, the shaft 30 includes threads 80 that engage with the main body member 20 such that rotation of the shaft translates the shaft with respect to the main body member. In other embodiments, the shaft can slide within the main body member and can be secured thereto at a desired location with a set screw. In yet other embodiments, the shaft can be moved with respect to the main body by a ratchet mechanism. In the embodiment shown, the shaft moves along an axis that intersects the tip 50. In other embodiments, such as that described with respect to FIG. 34, the shaft 30 and/or bone engagement member 40 is offset from tip 50.

As shown in FIG. 2, embodiments of the bone positioning device can have a bone engagement member 40. In some embodiments, the bone engagement member includes a surface 90 configured to contact a bone, such as a metatarsal or a cuneiform. In the embodiment shown, the surface 90 is concave. Such a surface is adapted to promote surface contact with a generally cylindrical bone, such as a metatarsal. Other embodiments of surface shapes include planar surfaces and V-shaped surfaces. When using a concave or V-shaped bone engagement member 40, the sidewalls of the concavity or V-shaped groove may be symmetrical or asymmetrical. In a symmetrical configuration, the bottom of the concavity or groove can be centered between upwardly extending sidewalls configured to receive a bone. Each sidewall can extend upwardly to the same height and/or at the same slope. In the asymmetrical configuration, one sidewall can have a different configuration than the opposing sidewall. For example, one of the sidewalls may extend upwardly from the bottom of the concavity or groove to a lower height than the opposing sidewall. As another example, one sidewall may extend upwardly at a different angle than the opposing sidewall. The asymmetrical configuration can be useful for applying a force that is biased laterally instead of only being linear toward tip 50.

In some embodiments, bone engagement member 40 includes a pin or a clamp. Independent of whether bone engagement member 40 includes such pin or clamp, the bone engagement member can engage an anatomical feature of a bone, such as a ridge (e.g., a medial ridge of a first metatarsal). In such embodiments, the engagement generally prohibits rotational movement of the bone with respect to the bone engagement member. In other embodiments, bone may be allowed to rotate with respect to the bone engagement member.

In the embodiment shown, the bone engagement member 40 is provided on an end of the shaft 30. In the embodiment of the shaft shown having threads 80, the bone engagement member 40 can be rotatably coupled to the shaft 30. In such embodiments, as the shaft is rotated relative to the main body member the bone engagement member 40 may or may not rotate with respect to the main body member even as it translates with respect to the main body member along with the shaft 30 and rotates with respect to the shaft. The bone engagement member may oscillate about the shaft 30, but generally does not rotate with respect to bone after contact with the bone.

FIGS. 3A-C depict a tip 50 of bone positioning guide 10, which can be at a second end 70 of the main body member opposite the first end. The tip 50 can be useful for contacting a bone, generally a bone distinct from a bone contacting the bone engagement member. For example, if the bone engagement member is in contact with a first metatarsal, the tip can be in contact with a metatarsal other than the first metatarsal (e.g., the second, third, fourth, or fifth metatarsal). In some embodiments, the tip is tapered to facilitate percutaneous insertion and contact with bone. The tip can also include a textured surface 100, such as serrated, roughened, cross-hatched, knurled, etc., to reduce slippage between the tip and bone. In the embodiment shown, the tip further includes a stop 110 to limit a depth of insertion. The shape of the tip can be configured to stably contact bone. For example, FIG. 3B shows a side view of the bone positioning guide with a generally straight tip 50, while FIG. 3C shows a side view of the bone positioning guide with a nonlinear tip 50 (e.g., a tip that is angled or curved). In some embodiments, the tip is configured to restrict translational movement between it and a bone, but to allow rotational movement between it and the bone.

As shown in FIG. 4, bone positioning guide 10 can also include an actuator (e.g., a knob or a handle) 120 to actuate the mechanism, in this embodiment associated with the shaft. In the embodiment shown, the actuator can be useful for allowing a user to rotate the shaft with respect to the main body member 20. Also as shown in FIG. 4, the actuator, shaft, and bone engagement member may include a cannulation 130 to allow the placement of a fixation wire (e.g., K-wire) through these components and into contact with or through a bone engaged with the bone engagement member. For example, the fixation wire can be placed into the bone engaged with bone engagement member 40 to fix the position of the bone engagement member with respect to the bone. In another example, the fixation wire can be placed through the bone in contact with the bone engagement member and into an adjacent bone to maintain a bone position of the bone in contact with the bone engagement member and the adjacent bone.

In other embodiments, the mechanism to urge the bone engagement member and the tip towards each other can include a tenaculum or tong structure. In such embodiments, the guide can include a first shaft pivotably connected to a second shaft. A first end of each shaft can include an actuator, such as a handle. A second end of the first shaft can include a bone engagement member, as described above. And a second end of the second shaft can include a tip, as described above. In use, the actuator can be actuated (e.g., squeezed together) to move the bone engagement member and the tip closer together to position bone. Other embodiments of this type may include another set of shafts and another pivoting connection such that the bone engagement member and tip translate towards each other when the actuator is actuated.

In other embodiments, the mechanism to urge the bone engagement member and the tip towards each other can include a rack and pinion structure. In such embodiments, the rack can include a tip, as described above. And the pinion can include a bone engagement member, as described above, and an actuator (e.g., a knob). In use, the actuator can be actuated (e.g., turned about an axis generally perpendicular to a direction of travel) to move the bone engagement member and the tip closer together to position bone.

Embodiments of the bone positioning guide may include any suitable materials. In certain embodiments, the bone positioning guide is fabricated from a radiolucent material such that it is relatively penetrable by X-rays and other forms of radiation, such as thermoplastics and carbon-fiber materials. Such materials are useful for not obstructing visualization of bones using an imaging device when the bone positioning guide is positioned on bones.

Embodiments of the bone positioning guide can be useful in operation for temporarily positioning a bone or bones during a medical procedure. Bone positioning can be useful, for instance, to correct an anatomical misalignment of bones and temporarily maintain an anatomically aligned position, such as in a bone alignment and/or fusion procedure. In some embodiments, the bone positioning guide is capable of reducing an angle between the first metatarsal and the second metatarsal from over 10 degrees (e.g., up to about 35 degrees) to about 10 degrees or less (e.g., to about 1-5 degrees), including to negative angles of about −5 degrees. In some embodiments, the bone positioning guide is also capable of rotating the first metatarsal about its long axis with respect to the medial cuneiform from a rotational angle of over 4 degrees to a rotational angle of less than 4 degrees (e.g., to about 0 to 2 degrees).

In some embodiments, a bone preparation guide may be provided to facilitate the preparation of a bone. The bone preparation guide can be provided with a bone positioning guide, or either device can be provided or used independently. An example of a bone preparation guide 150 is shown in FIG. 5. In some embodiments, the bone preparation guide 150 includes a body 154 defining a first guide surface 160 to define a first preparing plane and a second guide surface 164 to define a second preparing plane. A tissue removing instrument (e.g., a saw, rotary bur, osteotome, etc., not shown) can be aligned with the surfaces to remove tissue (e.g., remove cartilage or bone and/or make cuts to bone). The first and second guide surfaces 160, 164 can be spaced from each other by a distance, (e.g., between about 2 millimeters and about 10 millimeters, such as between about 4 and about 7 millimeters). In the embodiment shown, the first and second guide surfaces are parallel, such that cuts to adjacent bones using the guide surfaces will be generally parallel.

In some embodiments, as shown in FIG. 5, a first facing surface 166 is positioned adjacent the first guide surface 160 and/or a second facing surface 168 is positioned adjacent the second guide surface 164. In such embodiments, the distance between the first guide surface and the first facing surface defines a first guide slot, and the distance between the second guide surface and the second facing surface defines a second guide slot. Each slot can be sized to receive a tissue removing instrument to prepare the bone ends. The first and second slots may be parallel or skewed. In the illustrated embodiment, the facing surfaces each contain a gap, such that the surface is not a single, continuous surface. In other embodiments, the facing surfaces can be a single, continuous surface lacking any such gap.

An opening 170 can be defined by the body 154 between the first and second guide surfaces. The opening can be an area between the guide surfaces useful for allowing a practitioner to have a visual path to bones during bone preparation and/or to receive instruments. In the embodiment shown, the opening extends across the body and a distance from a surface 172 opposite of the first facing surface 166 to a surface 174 opposite of the second facing surface 168.

The embodiment shown also includes a first end 176 extending from the body 154 in a first direction and a second end 178 extending from the body in a second direction. The second direction can be different than the first direction (e.g., an opposite direction). As shown, each of the first end and the second end can include at least one fixation aperture 180 configured to receive a fixation pin (not shown in FIG. 5) to secure the guide to a bone. As shown, such apertures may extend through the end at a vertical or skewed angle relative to a top surface of the guide.

The bone preparation guide 150 can also include a first adjustable stabilization member 182 engaged with the first end 176. In some embodiments, the bone preparation guide can include a second adjustable stabilization member 184 engaged with the second end 178. Each of the members can be threaded and engage a threaded aperture defined by the ends. The elevation of each end can be adjusted with respect to a bone by adjusting the stabilization member. In some embodiments, as shown, the stabilization members are cannulated such that they can receive a fixation pin.

As shown in FIGS. 6A and 7, the bone preparation guide can also include a spacer 188 extending downward from the body 154 and configured to be placed into a joint. In some embodiments, the spacer 188 is selectively engageable with the body. The spacer can have a first portion 190 configured to extend into a joint space and a second portion 192 engageable with the body 154. In the embodiment shown, the spacer can be received within opening 170, such that the spacer extends from the body in between the first and second guide surfaces. Such a spacer can be useful for positioning the body at a desired position with respect to a joint and for properly positioning the guide with respect to bones to be cut in more than one plane (e.g., three planes selected from more than one of a frontal plane, a transverse plane, and a sagittal plane). The distance between the spacer and the first guide surface can define a length of tissue removal (e.g., bone or cartilage to be cut) from a first bone, and the distance between the spacer and the second guide surface can define a length of tissue removal (e.g., bone or cartilage to be cut) from a second bone.

As shown in FIGS. 6A/B and 8, the bone preparation guide can also include a tissue removal location check member 194 engageable with the body 154 and configured to extend to a first bone and a second bone. The tissue removal location check member can have a first portion 196 configured to extend into contact with first and second bones and a second portion 198 engageable with the body. In the embodiments shown in FIGS. 6A and 8, the tissue removal location check member extends from the body at both the first and second guiding surfaces. In other embodiments, such as the embodiment shown in FIG. 6B, separate tissue removal location check members are provided for independent insertion into respective slots of the guide. Accordingly, embodiments of tissue removal location check members are useful for allowing a practitioner to see where a tissue removing instrument guided by the surfaces will contact the bone to be prepared.

Embodiments of the bone preparation guide can be useful in operation for guiding a preparation of a bone or bones at a targeted anatomy. Bone preparation can be useful, for instance, to facilitate contact between leading edges of adjacent bones, separated by a joint, or different portions of a single bone, separated by a fracture, such as in a bone alignment and/or fusion procedure.

Embodiments of the present invention also include methods for temporarily fixing an orientation of a bone or bones, for example, prior to or in conjunction with permanently fixing the orientation of the bone or bones. In general, the method of positioning a bone includes the steps of moving a bone from an anatomically misaligned position to an anatomically aligned position with respect to another bone and preparing an end of the moved bone and a facing end of another bone. In some embodiments, the end of at least one of the moved bone and the other bone is prepared after moving the bone into the aligned position. In certain embodiments, the bone is anatomically aligned in more than one plane with respect to another bone by applying a force to one bone at a single location, such that the bone both translates and rotates in response to the force. In certain embodiments, the moving step can be accomplished with a bone positioning device and/or the preparing step can be accomplished with a bone preparation guide, as described herein.

Figure 9A:
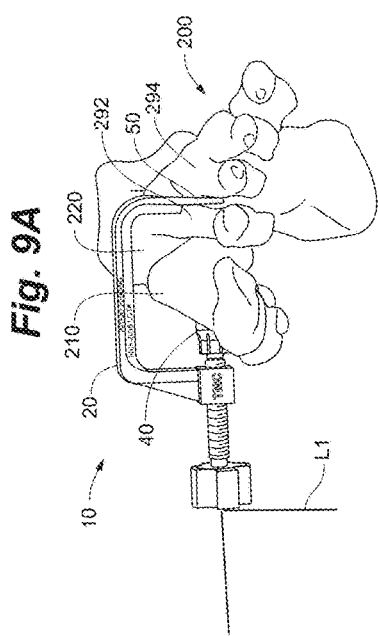
FIG. 9A is a front view of a bone positioning guide on a deformed foot in accordance with an embodiment of the invention.
Figure 9B:
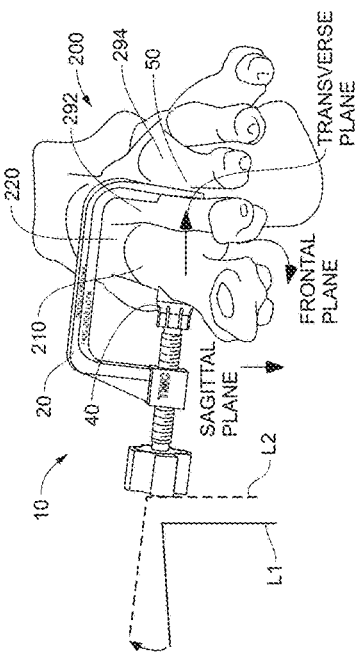
FIG. 9B is a front view of a bone positioning guide on a foot with a corrected alignment in accordance with an embodiment of the invention.

FIGS. 9A-B depict frontal views of a bone positioning guide 10 on a foot 200 having a first metatarsal 210, a medial cuneiform 220, a second metatarsal 292, and a third metatarsal 294. FIG. 9A depicts a foot 200 with an uncorrected bunion deformity, while FIG. 9B depicts the foot 200 with an alignment corrected by the bone positioning guide 10. Solid line L1 represents the starting location of the bone positioning guide 10 and dotted line L2 represents the finishing location of the bone positioning guide. As shown, as the bone positioning guide 10 is actuated it rotates with the first metatarsal 210 about an axis extending through the frontal plane as it pushes the first metatarsal 210 laterally in the transverse plane and plantarly in the sagittal plane. Accordingly, in this example, the position of the first metatarsal 210 is corrected with respect to the second metatarsal 292 generally in three planes by actuating a single bone positioning guide 10 to urge a bone engagement member 40 toward a tip 50. FIG. 10A shows a top view of a foot 200 with an uncorrected bunion deformity, while FIG. 10B shows a top view of the foot 200 with an alignment corrected by the bone positioning guide 10, emphasizing the rotational correction in the frontal plane and the lateral correction in the transverse plane.

Figure 11A:
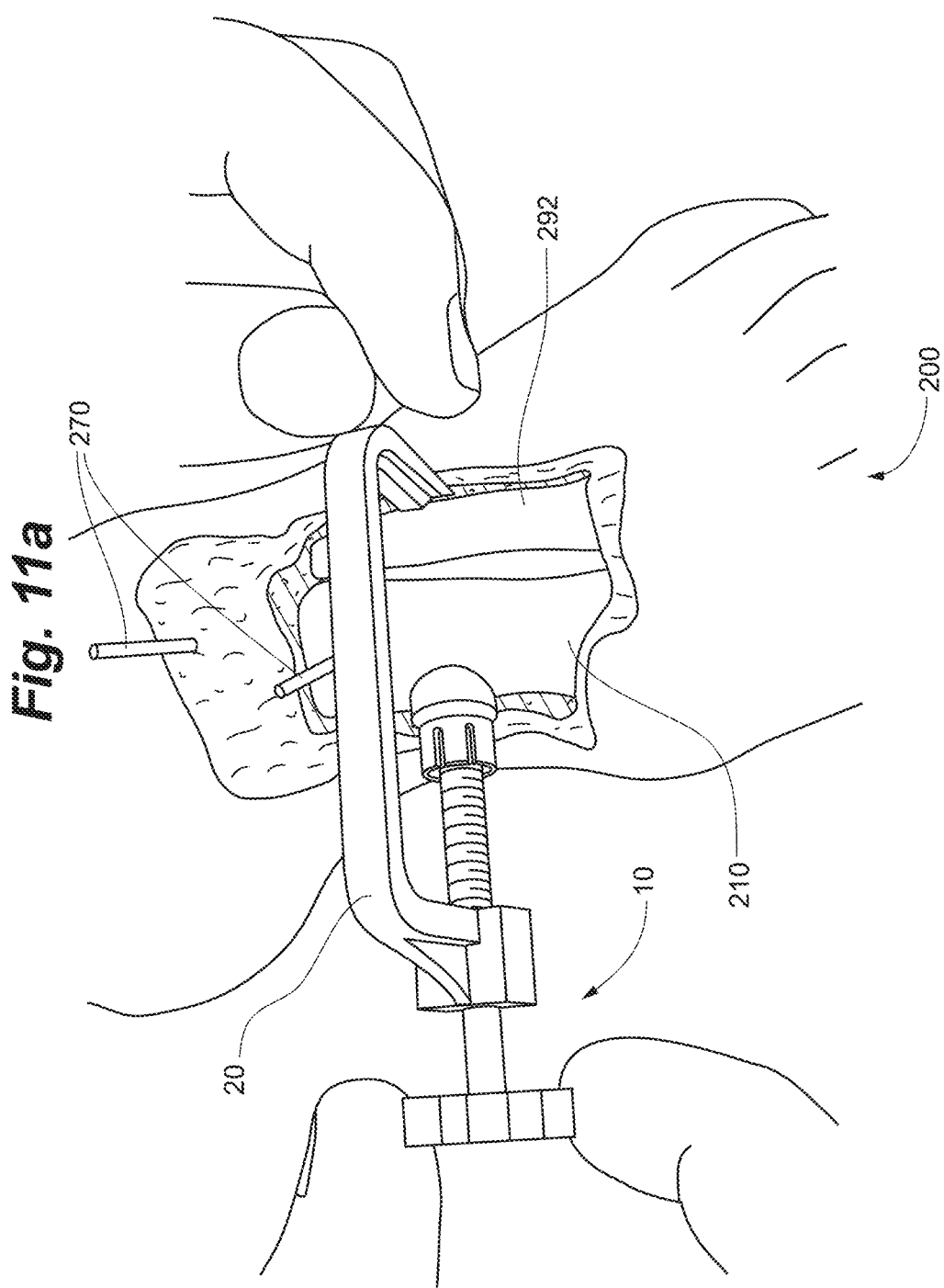
FIGS. 11A-C depict a sequence of a bone positioning operation using a bone positioning guide on a foot at first, second, and third positions in accordance with an embodiment of the invention.
Figure 11B:
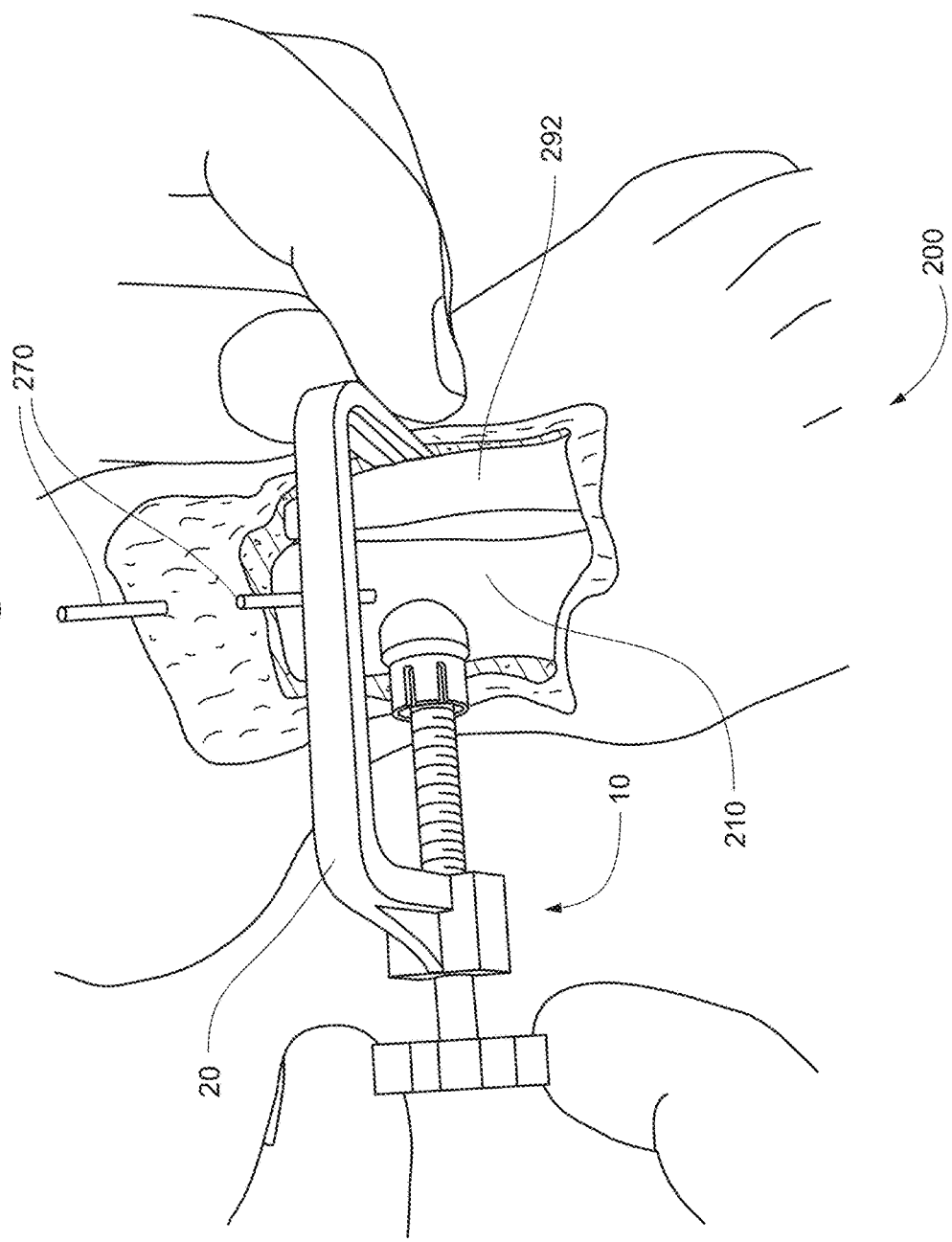
Figure 11C:
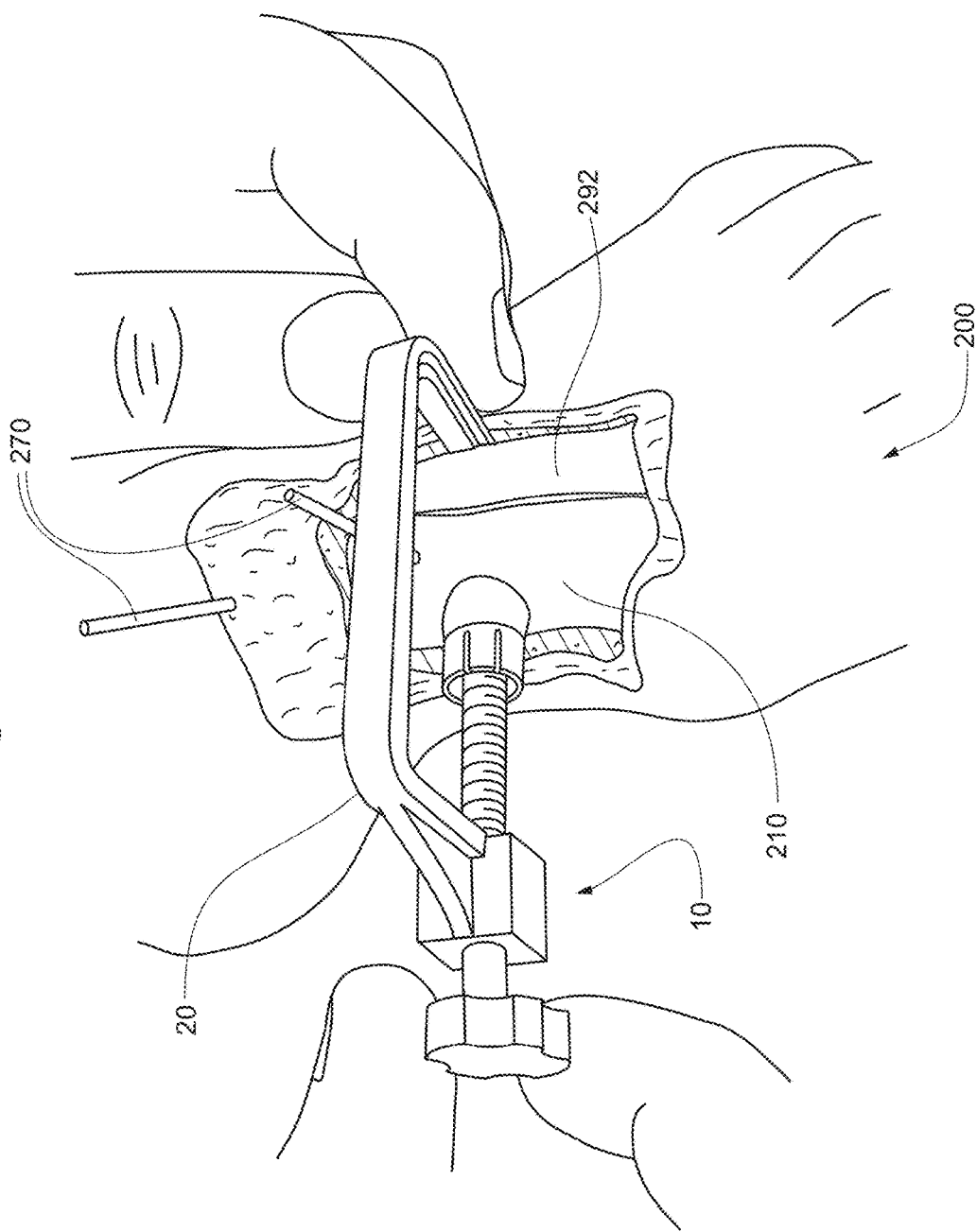

FIGS. 11A-C show three sequential images of a bone positioning guide 10 on a foot 200 positioning a first metatarsal 210 with respect to a second metatarsal 292. FIG. 11A represents the beginning of the procedure, FIG. 11B the middle, and FIG. 11C the end. The orientation of the pins 270 is useful for visualizing the amount of rotation of the first metatarsal 210 in each image. With respect to FIGS. 11A-C, it can be seen the bone positioning guide 10 and the first metatarsal 210 are rotating in the frontal plane in response to actuation of bone positioning guide 10. Further, the angle between the first metatarsal 210 and second metatarsal 292 is reduced, as the space that can be seen between the first and second metatarsals in FIG. 11A is eliminated in FIG. 11C.

Figure 12B:
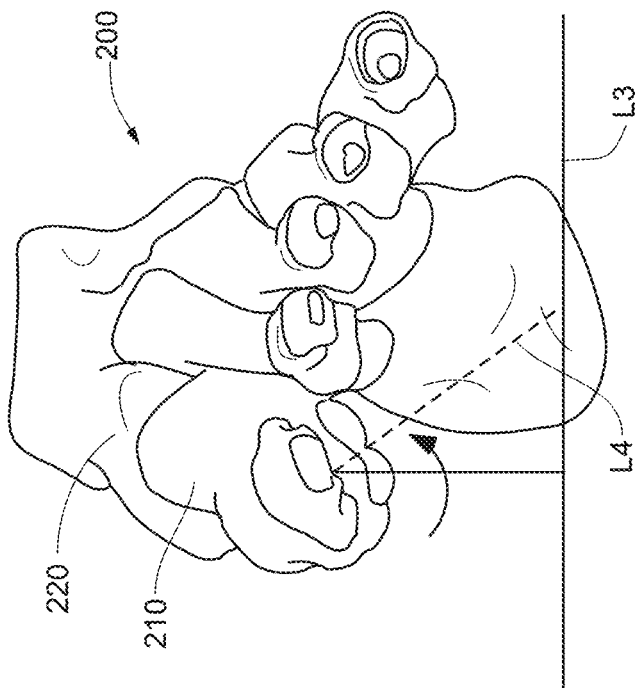
FIG. 12B is a front view of a foot with an isolated first metatarsal rotation bunion deformity.
Figure 12A:
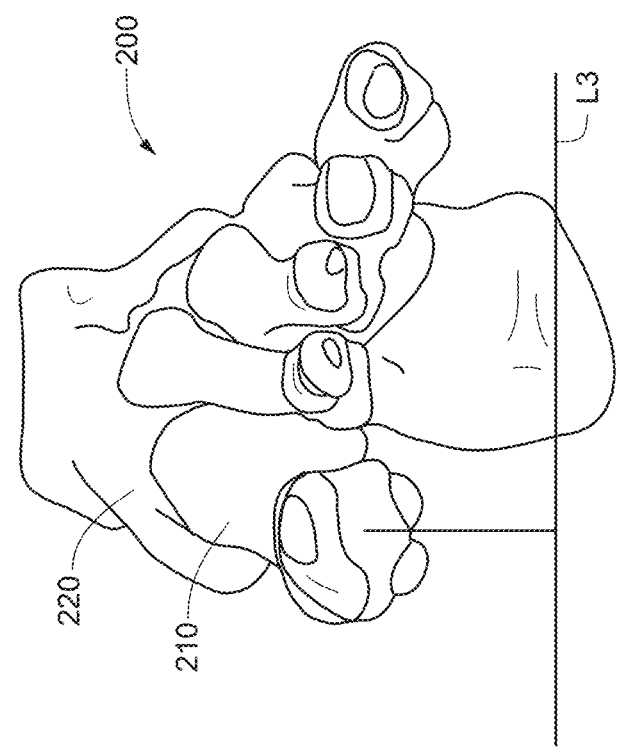
FIG. 12A is a front view of a foot with a normal first metatarsal position.

Each of the three potential planes of deformity will now be described in isolation. FIGS. 12A and 12B show frontal plane views of a foot 200. In FIG. 12A, the foot 200 is normal, while in FIG. 12B the foot is depicted with an uncorrected bunion deformity showing an isolated axial rotation of the first metatarsal 210. Solid line L3 indicates the alignment of the first metatarsal 210 relative to ground, while dotted line L4 in FIG. 12B indicates the extent of axial rotation in the frontal plane.

FIGS. 13A and 13B show transverse plane views of a foot 200. In FIG. 13A, the foot 200 is normal, while in FIG. 13B the foot is depicted with an uncorrected bunion deformity showing an isolated transverse plane first metatarsal 210 deviation. Solid line L5 indicates the alignment of the second metatarsal 292 and solid line L6 indicates the proper alignment of the first metatarsal 210 relative to the second metatarsal 292. The angle between these two lines forms the intermetatarsal angle (IMA). Dotted line L7 in FIG. 13B indicates the extent of transverse deviation.

Figure 14A:
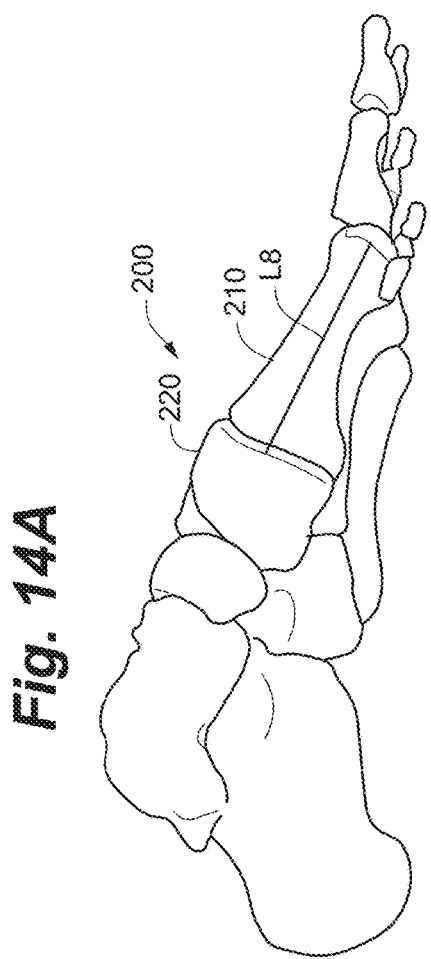
FIG. 14A is a side view of a foot with a normal first metatarsal position.
Figure 14B:
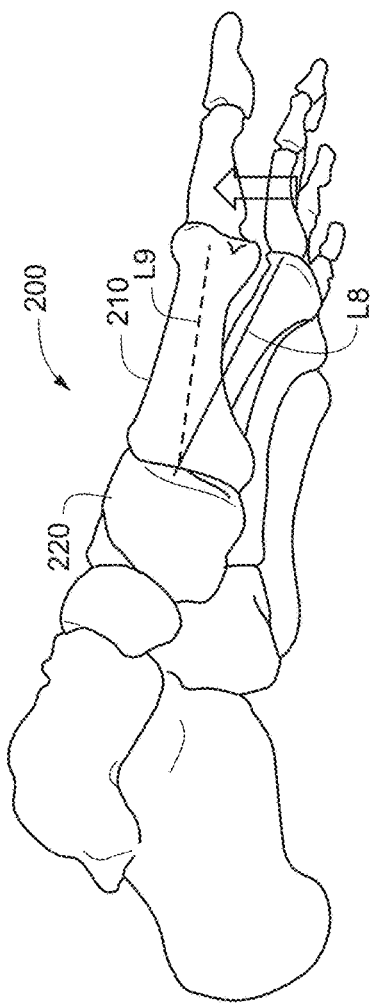
FIG. 14B is a side view of a foot with an isolated first metatarsal sagittal plane bunion deformity.

FIGS. 14A and 14B show sagittal plane views of a foot 200. In FIG. 14A, the foot 200 is normal, while in FIG. 14B the foot is depicted with an uncorrected bunion deformity showing an isolated sagittal deviation of the first metatarsal 210. Solid line L8 indicates the proper alignment of the first metatarsal 210, while dotted line L9 in FIG. 14B indicates the extent of sagittal deviation.

A specific embodiment of a method in accordance with an embodiment of the invention includes the steps of engaging a bone engagement member with a first bone, placing a tip of the bone positioning guide in apposition to a second bone, the second bone being different from the first bone, and moving the bone engagement member with respect to the tip to change the position of the first bone with respect to the second bone in more than one plane. In some embodiments, after alignment, at least one of an end of the first bone and a facing end of a third bone are prepared (e.g., only the end of the first bone or both the end of the first bone and the end of the second bone), optionally using a preparation guide.

Figure 15A:
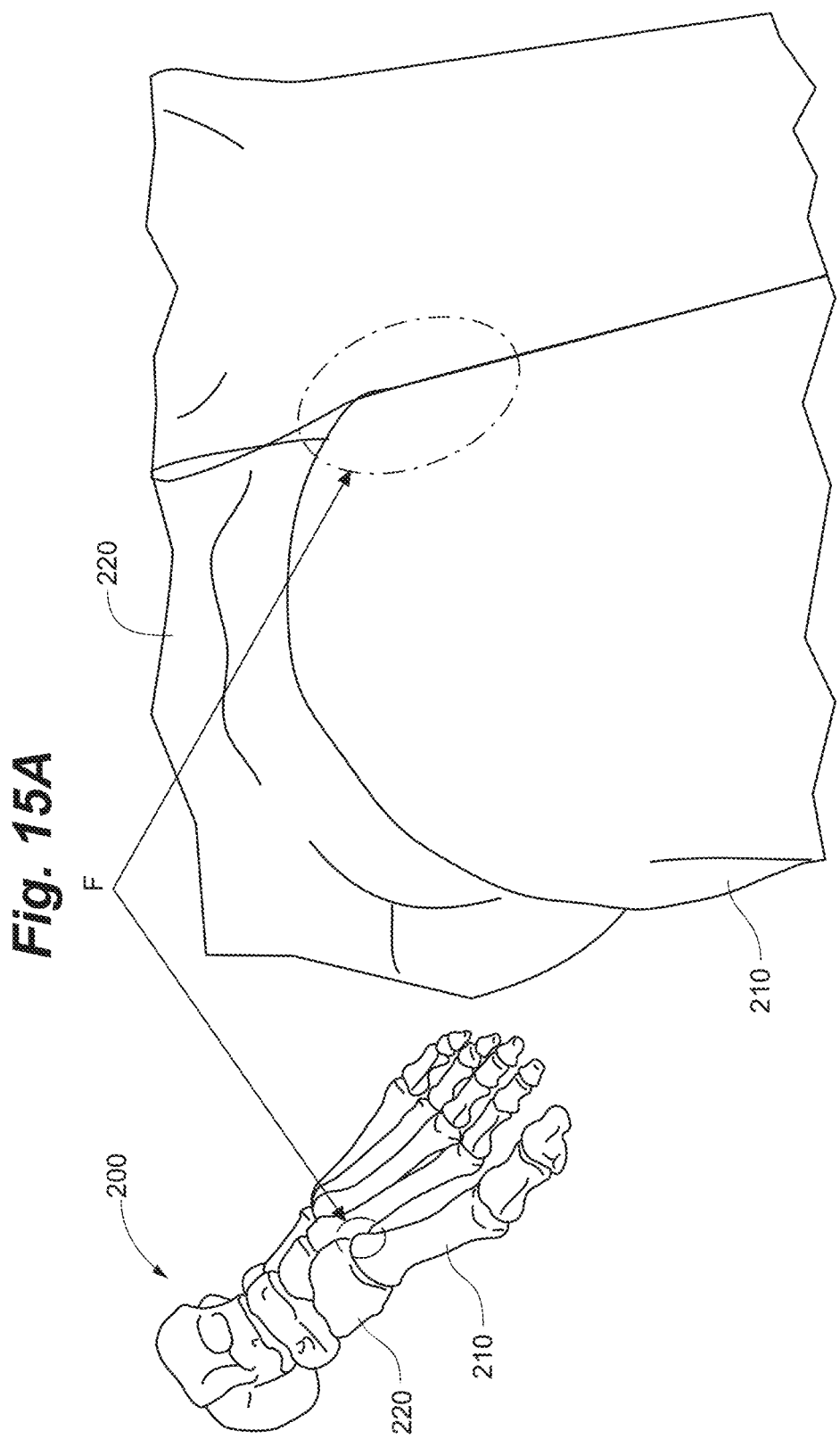
FIG. 15A is a perspective view and an enlarged view of a foot.
Figure 15B:
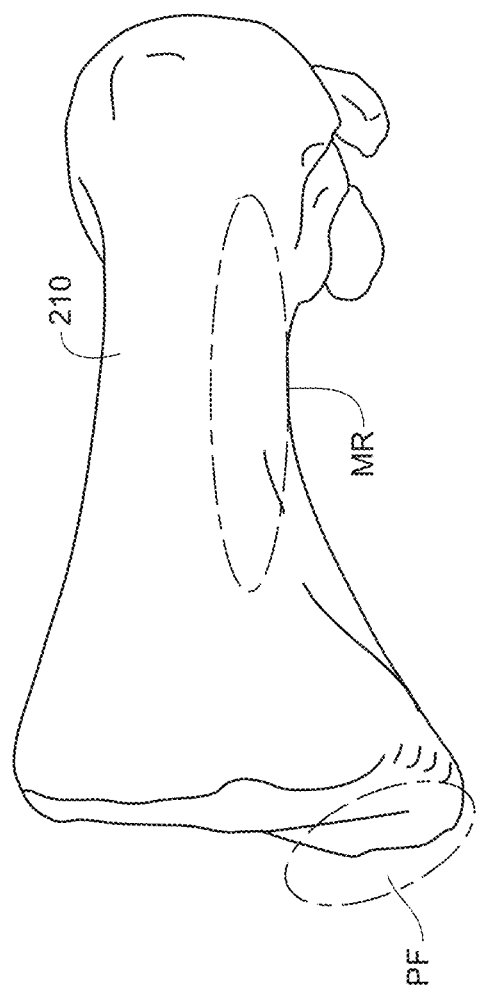
FIG. 15B is a perspective view of a first metatarsal.

In some embodiments, the method includes the step of mobilizing a joint for a corrective procedure. For example, after creating surgical access to the joint and before moving the bones into an aligned position, tissue can be released to allow a bone, such as a metatarsal, to rotate freely. In some embodiments, obstructing bone may be excised (e.g., a dorsolateral flare of the metatarsal base, a plantar flare of the metatarsal base (sometimes referred to as a plantar condyle), part of an end of a metatarsal facing a cuneiform, or osteophyte) to further promote free rotation by creating relatively flat surfaces with respect to a frontal plane. An example of a dorsolateral flare F on a first metatarsal 210 of a foot 200 is shown in FIG. 15A. An example of a plantar flare PF on a first metatarsal 210 is shown in FIG. 15B. FIG. 15B also depicts a medial ridge MR, which, in some embodiments, can be engaged by the bone engaging member of a bone positioning guide.

Embodiments of methods in accordance with the invention can also include steps performed after preparing the ends of the bones. For example, the ends of the bones may be placed in apposition and optionally compressed together and the position of the bones can be fixed with one or more bone fixation devices (e.g., compressing bone screw, bone plate, bone staple, external fixator, intramedullary implant or nail) prior to a closing of the surgical access to the joint.

An exemplary method will now be described with respect to FIGS. 16-27 depicting a foot 200 having a first metatarsal 210, a medial cuneiform 220, and a second metatarsal 292. Note, unless otherwise indicated, the steps described need not be carried out in the order described.

Figure 16:
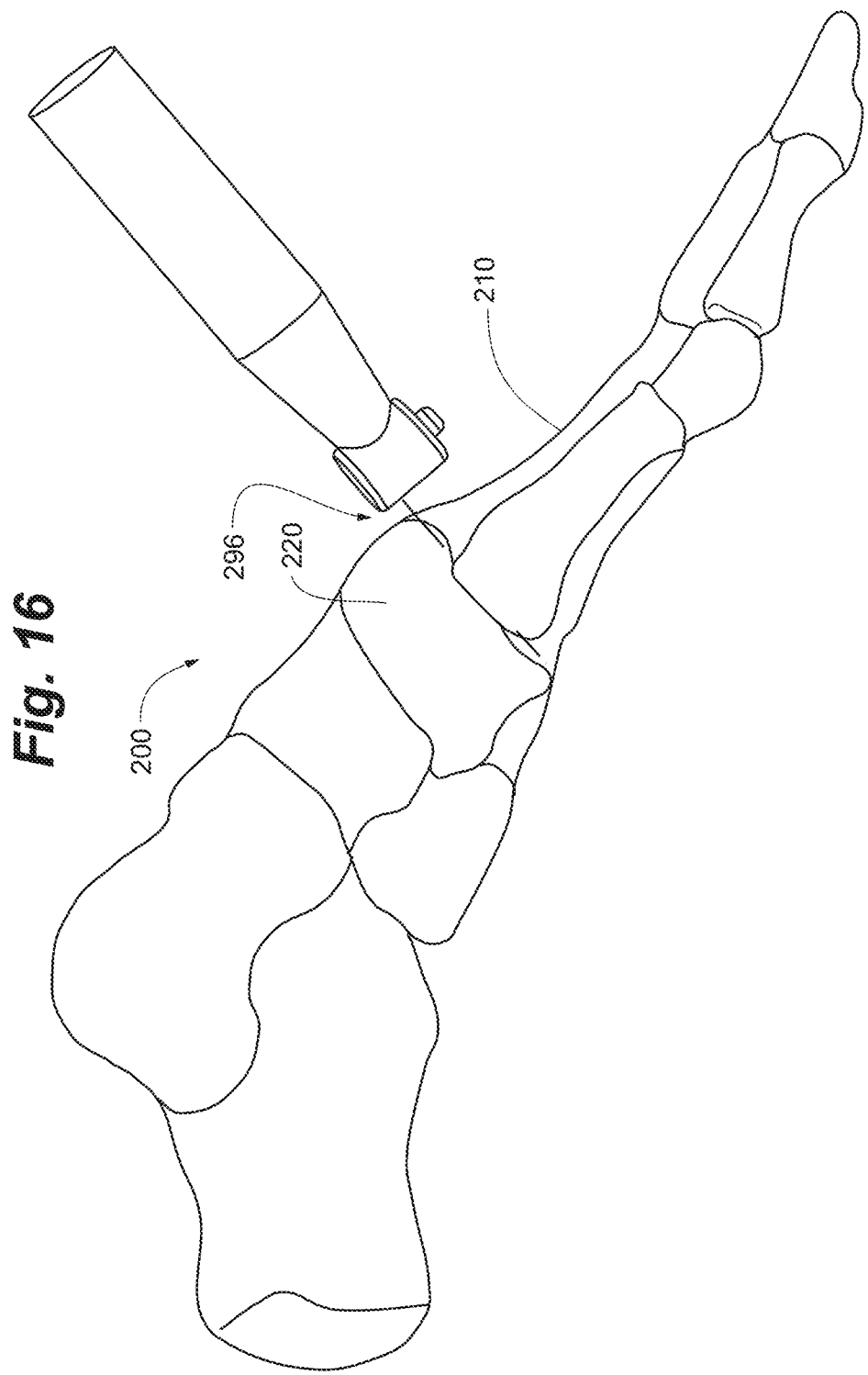
FIG. 16 is a side perspective view of a foot depicting a bone preparation instrument inserted into a joint.

After customary surgical preparation and access, a bone preparation instrument 296 can be inserted into the joint (e.g., first tarsal-metatarsal joint) to release soft tissues and/or excise the plantar flare from the base of the first metatarsal 210, as shown in FIG. 16. Excising the plantar flare may involve cutting plantar flare off the first metatarsal 210 so the face of the first metatarsal is generally planar. This step helps to mobilize the joint to facilitate a deformity correction. In some embodiments, the dorsal-lateral flare of the first metatarsal may also be excised to create space for the deformity correction (e.g., with respect to rotation of the first metatarsal). In certain embodiments, a portion of the metatarsal base facing the medial cuneiform can be removed during this mobilizing step.

Figure 17:
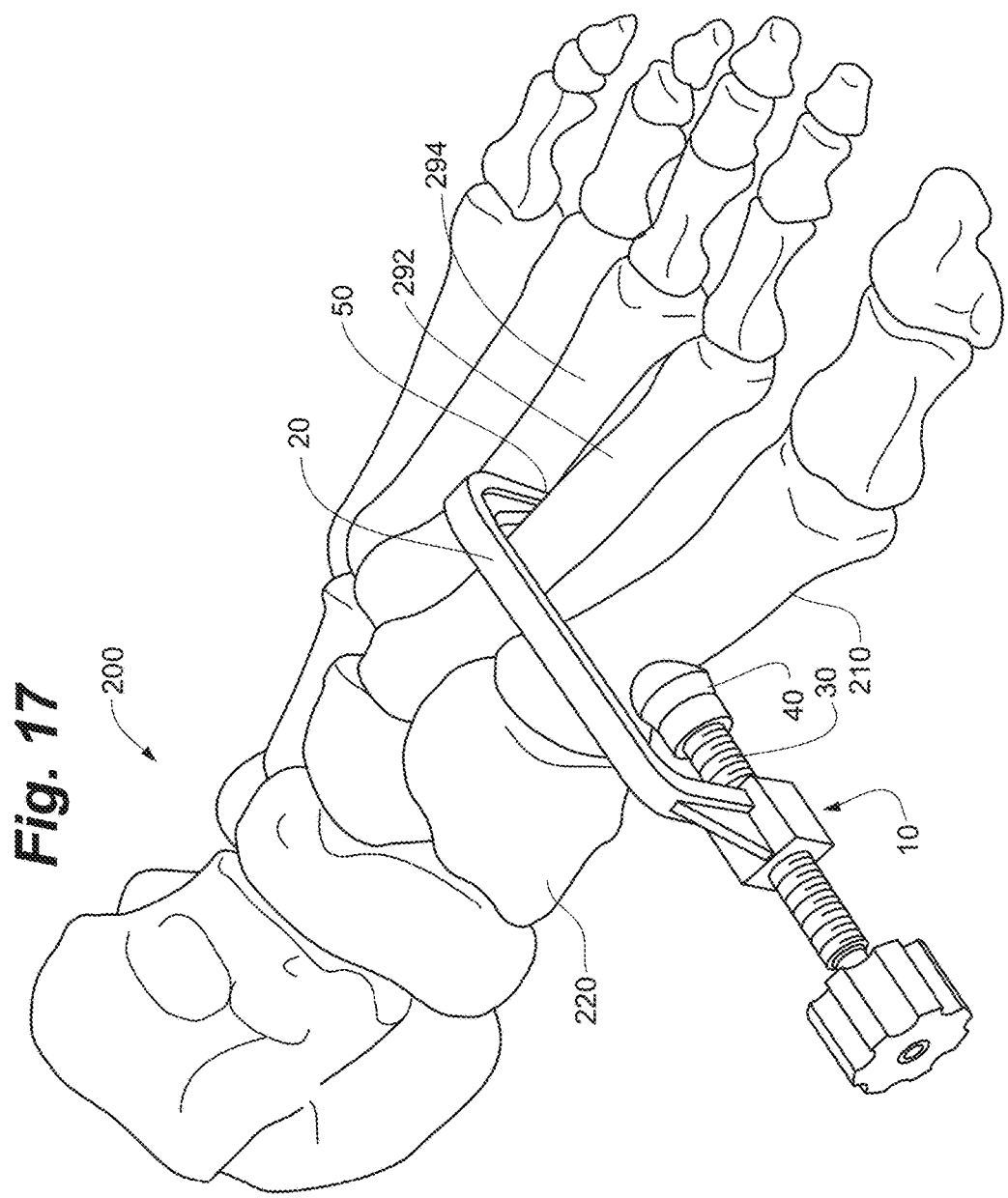
FIG. 17 is a perspective view of a foot depicting a bone positioning guide on the foot prior to an alignment of a first metatarsal.

An incision can be made and a tip 50 of a bone positioning guide 10 can be inserted on the lateral side of a metatarsal other than the first metatarsal 210, such as the second metatarsal 292. As shown in FIG. 17, the tip can be positioned proximally at a base of the second metatarsal 292 and a third metatarsal 294 interface. A surface of a bone engagement member 40 can be placed on the proximal portion of the first metatarsal 210. In some embodiments, the bone engagement member engages a medial ridge of the first metatarsal 210. As shown, the body 20 of the positioning guide can be generally perpendicular to the long axis of the second metatarsal 292.

Figure 18:
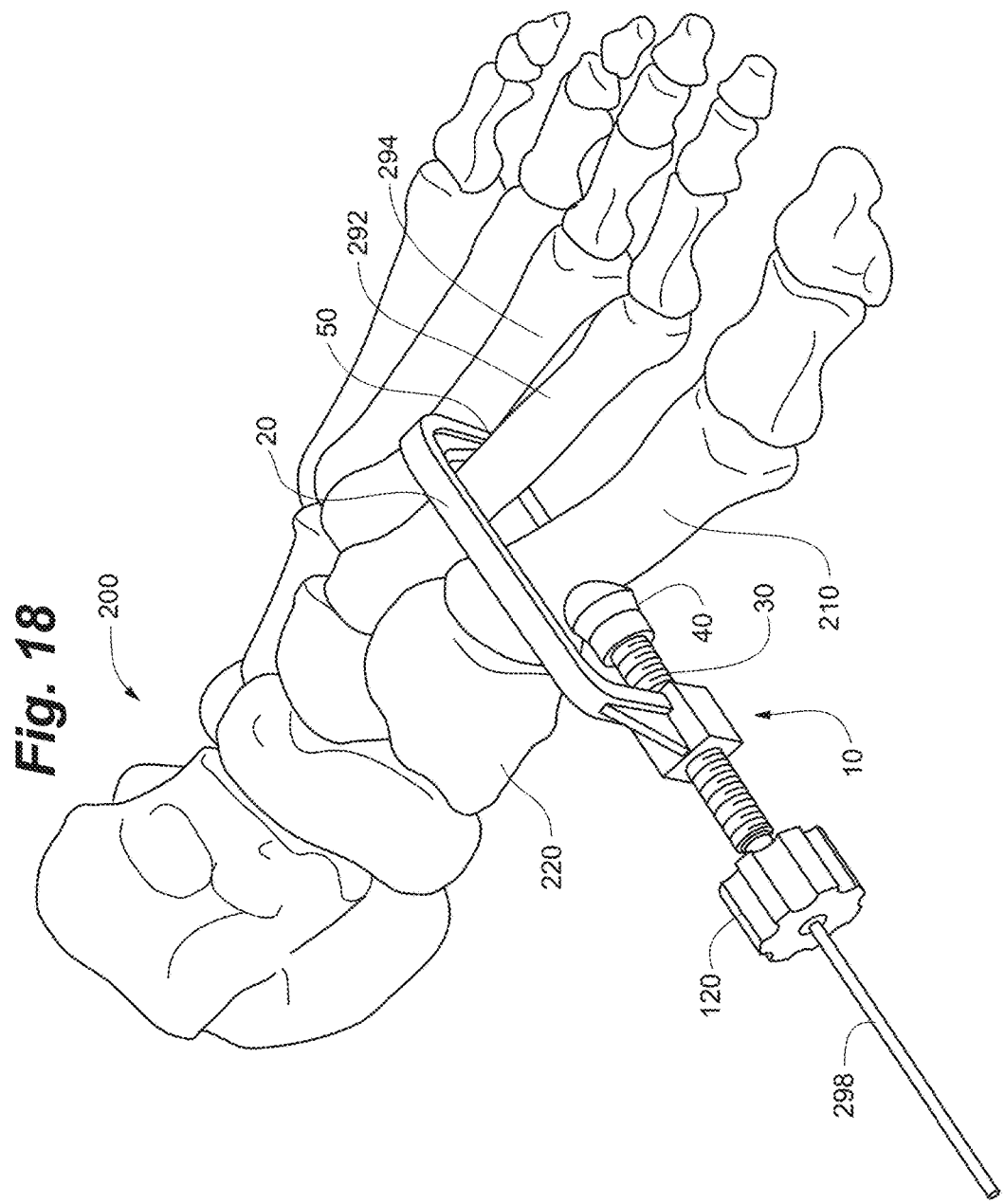
FIG. 18 is a perspective view of a foot depicting a bone positioning guide on the foot after an alignment of a first metatarsal.

As depicted in FIG. 18, the actuator 120 can be actuated to extend the shaft 30 to reduce the angle (transverse plane angle between the first metatarsal and the second metatarsal) and rotate the first metatarsal about its axis (frontal plane axial rotation). The first metatarsal 210 can be properly positioned with respect to the medial cuneiform 220 by moving the bone engagement member 40 with respect to the tip 50. In some embodiments, such movement simultaneously pivots the first metatarsal with respect to the cuneiform and rotates the first metatarsal about its longitudinal axis into an anatomically correct position to correct a transverse plane deformity and a frontal plane deformity. In certain embodiments, body 20 rotates in a generally lateral direction during this step. In some embodiments, fixation pins (not shown in FIG. 18) can be inserted into the bones prior to the positioning step (e.g., freehand or using apertures in the guide as a template), and can be used to impart additional force (transverse, sagittal, and/or frontal plane rotational) to the first metatarsal 210, if desired. The bone positioning guide 10 can hold the desired position of the first metatarsal 210 with respect to the second metatarsal 292. After the desired correction is achieved, a fixation wire 298 can be inserted through a cannulation in the shaft 30 and driven into the first metatarsal 210 and the second metatarsal 292 to hold the corrected position.

As depicted in FIG. 19, a joint spacer 188 can be positioned within the joint between the first metatarsal and the medial cuneiform.

As shown in FIG. 20, a bone preparation guide 150 can be placed over the joint spacer 188 and engaged with the joint spacer to set a position and orientation of the bone preparation guide relative to the joint. As shown, the bone preparation guide 150 can be positioned proximal to the bone positioning guide 10 in longitudinal alignment with the long axis of the first metatarsal 210 and the medial cuneiform 220, generally on the dorsal or dorsal-medial surface. In other embodiments, the spacer 188 is positioned after the guide 150 is provisionally placed on the bones. In yet other embodiments, bone preparation guide 150 and joint spacer 188 are placed simultaneously. In still other embodiments, bone preparation guide 150 is placed on the bones without using joint spacer 188 to aid with positioning.

Figure 21B:
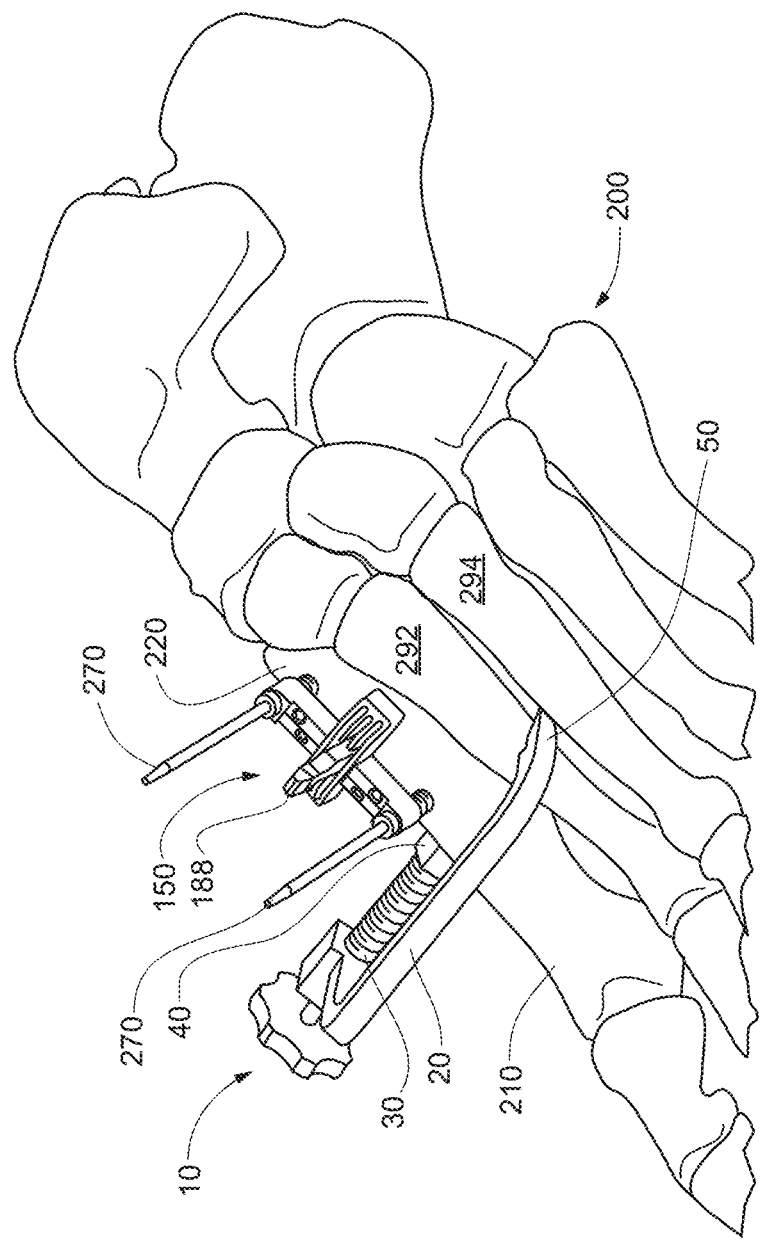
FIG. 21B is another perspective view of a foot depicting a bone positioning guide on the foot after an alignment of a first metatarsal and a positioning of a bone preparation guide with pins.

As depicted in FIGS. 21A and 21B, one or more fixation pins 270 can be inserted into apertures of the bone preparation guide 150 to secure the guide to the first metatarsal 210 and the medial cuneiform 220. As shown, some pins 270 can be inserted at an angle or in a converging orientation to help prevent movement of the bone preparation guide 150 during a tissue removing step. As shown, two of the pins 270, one on the first metatarsal and one on the medial cuneiform, are parallel to allow the bone preparation guide 150 to be removed from the foot without removing all the pins. After insertion of the pins 270, the spacer 188 can optionally be removed in embodiments having a selectively engageable spacer (e.g., a joint spacer 188 that is physically removable from bone preparation guide 150).

In some embodiments, the location of the intersection of the tissue removing instrument and the bone to be prepared is confirmed before bone preparation. In one embodiment, a tissue removing instrument location check member can be engaged with the preparation guide to visually confirm where a tissue removal instrument will contact the bone. In another embodiment, a tissue removal instrument is engaged with the preparation guide to visually confirm where the instrument will contact the bone. In either embodiment, such visual confirmation can include the use of an imaging device, such as an X-ray. If the position of the preparation guide is correct, additional fixation pins may be inserted through the apertures (e.g., angled apertures) to further fix the position of the preparation guide with respect to the first metatarsal and the medial cuneiform. In some embodiments, the spacer is reattached prior to further bone preparation steps.

In some embodiments, the end of the first metatarsal 210 facing the medial cuneiform 220 can be prepared with a tissue removing instrument 296 guided by a guide surface of bone preparation guide 150 (e.g., inserted through a slot defined by a first guide surface and a first facing surface). In some embodiments, the first metatarsal 210 end preparation is done after the alignment of the bones, e.g., by actuating bone positioning guide 10 before preparing the end of first metatarsal 210. In other embodiments, the first metatarsal 210 end preparation is done before the alignment of the bones, e.g., by preparing the end of the first metatarsal 210 before actuating bone positioning guide 10.

Figure 22:
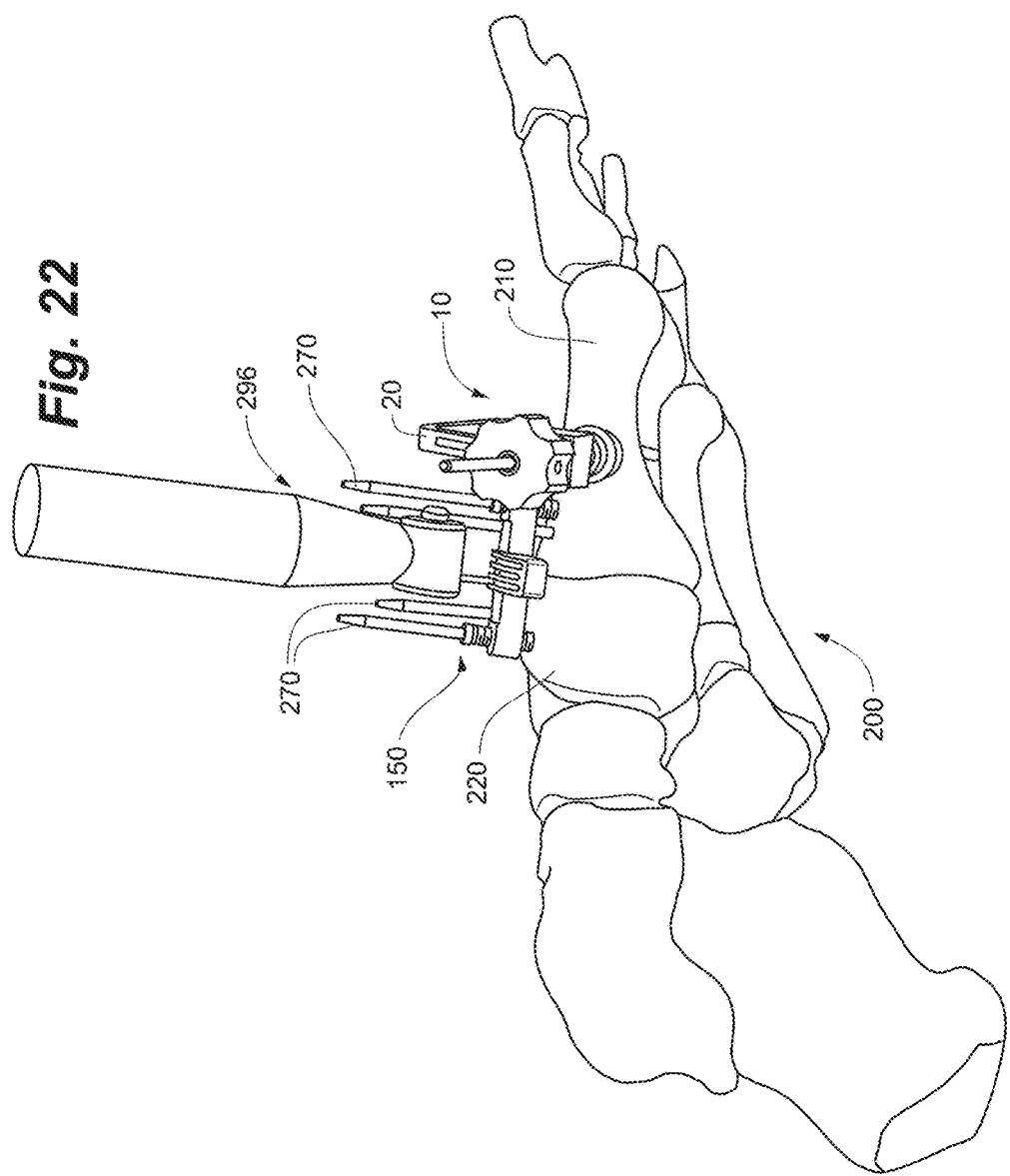
FIG. 22 is a perspective view of a foot depicting a bone preparation instrument preparing a bone of the foot guided by a guide surface of a bone preparation guide.

In addition, as shown in FIG. 22, the end of the medial cuneiform 220 facing the first metatarsal 210 can be prepared with the tissue removing instrument 296 guided by a guide surface of bone preparation guide 150 (e.g., inserted through a slot defined by a second guide surface and a second facing surface). In some embodiments, the medial cuneiform 220 end preparation is done after the alignment of the bones. In yet other embodiments, the medial cuneiform 220 end preparation is done before the alignment of the bones. In embodiments that include cutting bone or cartilage, the cuneiform cut and the metatarsal cut can be parallel, conforming cuts. In the specific embodiment shown in FIG. 22, a saw blade can be inserted through a first slot to cut a portion of the medial cuneiform and the saw blade can be inserted through a second slot to cut a portion of the first metatarsal (e.g., in some embodiments the medial cuneiform can be cut before the first metatarsal). Accordingly, in the embodiment shown, the cuts to both the first metatarsal and the medial cuneiform were preformed after the first metatarsal was positioned.

Figure 23:
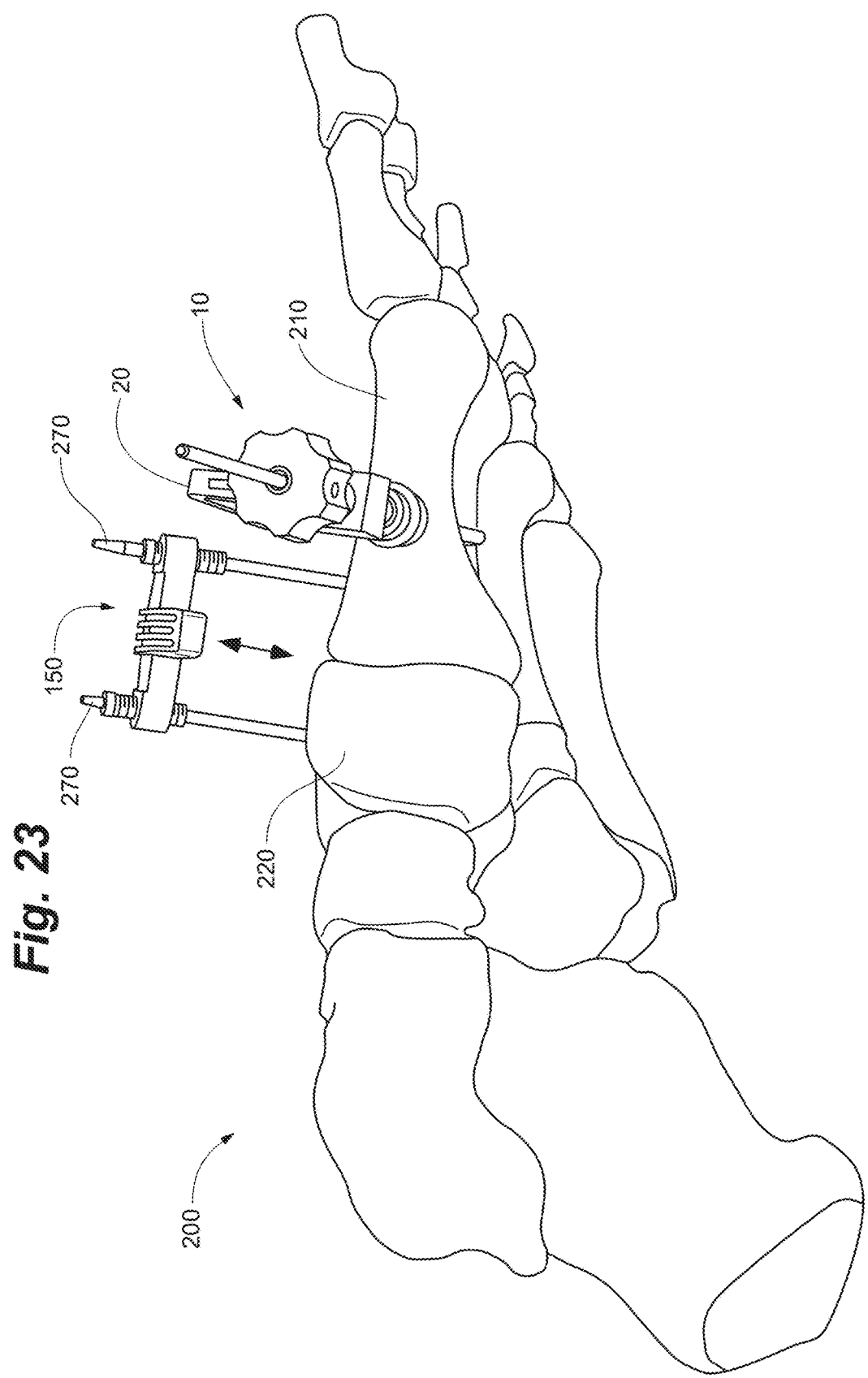
FIG. 23 is a perspective view of a foot depicting a bone positioning guide on the foot and a removal of a bone preparation guide.

Any angled/converging pins can be removed and the bone preparation guide 150 can be lifted off the parallel pins 270, as shown in FIG. 23. The parallel pins can be referred to as "reference pins" which can serve as a reference in later steps to ensure that the corrected alignment of the first metatarsal 210 has been maintained. The joint spacer can also be removed before, after, or simultaneously with the bone preparation guide. In some embodiments, the bone positioning guide 10 is also removed from the foot.

The tissue (e.g., bone or cartilage slices) from the first metatarsal and the medial cuneiform can be removed from the joint site and the joint surfaces can be fenestrated, if desired. If the bone positioning guide was taken off the foot, it can be put back on, as shown in FIG. 24, before the additional steps discussed below.

After preparation, the ends of the two bones can be placed in apposition and optionally compressed together by provisionally fixating the joint. For example, the two bones may be placed in apposition by placing the cut end of the first metatarsal 210 in abutment with the cut end of the medial cuneiform 220. In some examples, the cut end of the first metatarsal 210 is placed adjacent to, and optionally in contact with, the cut end of the medial cuneiform 220.

As shown in FIG. 25, a compression pin, such as a threaded olive pin 300 can be inserted through the first metatarsal 210 and into the medial cuneiform 220 to provide compression and provisional fixation between the first metatarsal and the medial cuneiform. Additional compression pins can be inserted to provide additional stability. As shown, the parallel reference pins should be aligned during this step. In some embodiments, a practitioner checks for alignment of the parallel reference pins prior to insertion of the compression pin, and, if they are not aligned, adjusts the position of the first metatarsal until desired alignment is achieved.

Figure 26A:
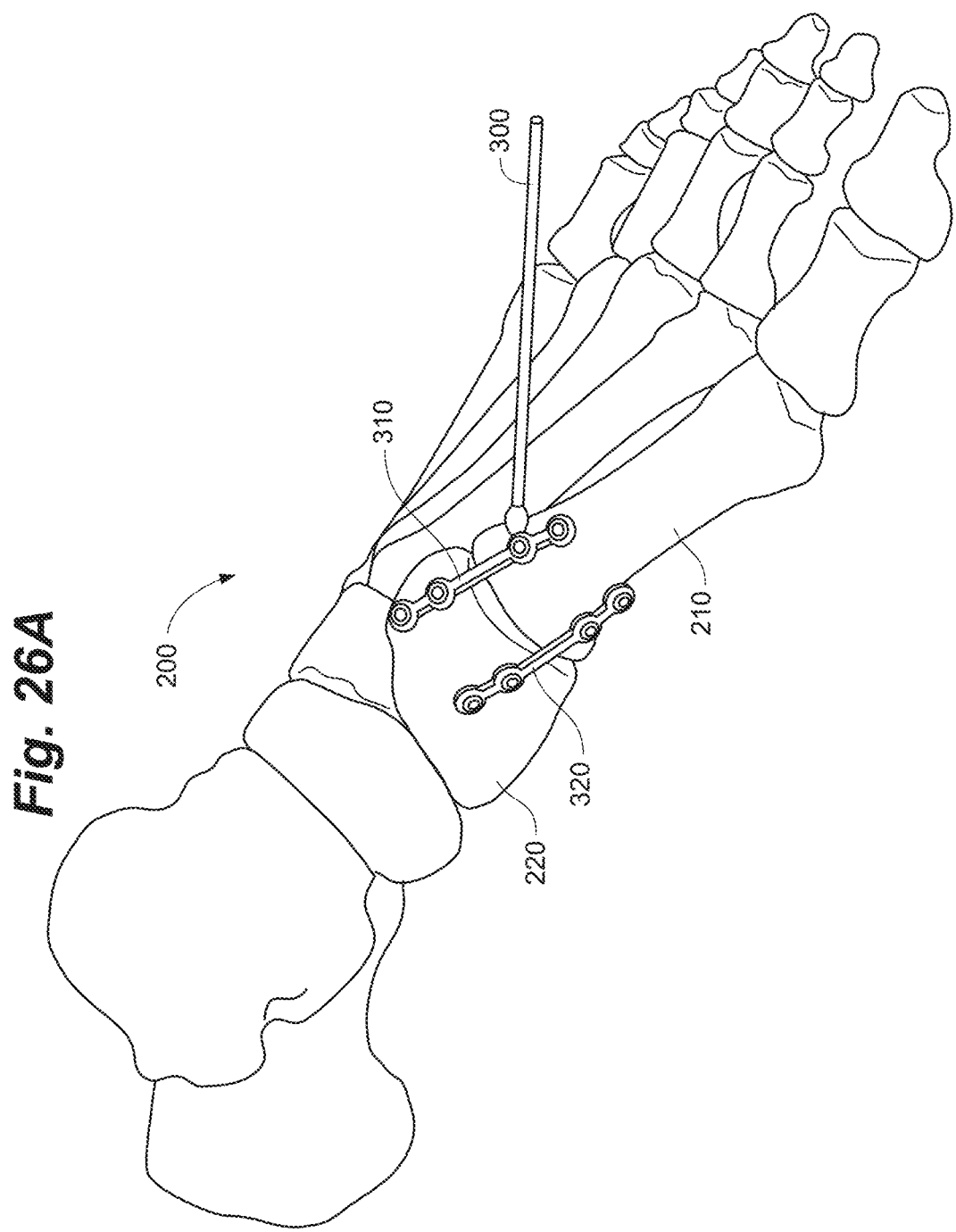
FIG. 26A is a side perspective view of a foot depicting bone plates across a joint between first and second bones and a compression pin in accordance with an embodiment of the invention.

Although they can be left in place, in some embodiments the parallel reference pins and bone positioning guide can be removed and a bone fixation device (e.g., two bone plates positioned in different planes, as shown) can be applied to stabilize the joint for fusion. FIG. 26A shows a first bone plate 310 positioned on a dorsal-medial side of the first metatarsal and medial cuneiform and a second bone plate 320 positioned on a medial-plantar side of the first metatarsal and the medial cuneiform. In other embodiments, such as the embodiment shown in FIG. 26B, the second bone plate 320 can be a helical bone plate positioned from a medial side of the cuneiform to a plantar side of the first metatarsal across the joint space. The plates can be applied with the insertion of bone screws.

As shown in FIG. 27, the compression pin can be removed and the incision can be closed.

FIGS. 28 A/B and 29A/B include examples of anatomically misaligned metatarsals and metatarsals that have been anatomically aligned using methods and/or instruments in accordance with the invention. FIG. 28A shows a left foot pre-operation and post-operation, while FIG. 28B shows a right foot pre-operation and post-operation. As can be seen from a comparison of the pre-operative images to the post-operative images, the patients' intermetatarsal angle (IMA) was significantly reduced. FIGS. 29A and 29B show the correction of an axial rotation in a frontal rotational plane. FIG. 29 A shows a pre-operative image and a post-operative image of a right foot. Drawings of a metatarsal 210 are also provided to illustrate the rotation. The rotation of the metatarsal can be seen by the position of sesamoid bones 400, which are depicted as having been rotated under the first metatarsal 210 in the post-operative drawing. FIG. 29B shows pre-operative views of a left foot 200 and a right foot 200. Again, by comparing the location of the sesamoid bones 400 with respect to a reference location, such as ground, the planter surface of the foot, and/or a cuneiform, it can be seen this patient's metatarsal is rotated out of alignment.

Methods in accordance with embodiments of the invention can be useful for temporarily positioning a bone or bones. Bone positioning can be useful, for instance, to correct an anatomical misalignment of bones and temporarily maintain an anatomically aligned position, such as in a bone alignment and/or fusion procedure. In some embodiments, an "anatomically aligned position" means that an angle of a long axis of a first metatarsal relative to a long axis of a second metatarsal is about 10 degrees or less in the transverse plane or sagittal plane. In certain embodiments, anatomical misalignment can be corrected in both the transverse plane and the frontal plane. In the transverse plane, a normal intermetatarsal angle ("IMA") between a first metatarsal and a second metatarsal is less than about 9 degrees. An IMA of between about 9 degrees and about 13 degrees is considered a mild misalignment of the first metatarsal and the second metatarsal. An IMA of greater than about 16 degrees is considered a severe misalignment of the first metatarsal and the second metatarsal. In some embodiments, methods in accordance with the invention are capable of anatomically aligning the bone(s) by reducing the IMA from over 10 degrees to about 10 degrees or less (e.g., to an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal is axially rotated between about 4 degrees to about 30 degrees or more. In some embodiments, methods in accordance with the invention are capable of anatomically aligning the metatarsal by reducing the metatarsal rotation from about 4 degrees or more to less than 4 degrees (e.g., to about 0 to 2 degrees) by rotating the metatarsal with respect to the medial cuneiform.

While various embodiments of bone positioning and preparing guide systems and methods have been described, is should be appreciated that the concepts of the disclosure can be altered in practice, e.g., based on the needs of the clinician, the patient undergoing the bone repositioning procedure, the specific anatomy being treated, and/or the target clinical outcome. As one example, the described systems and techniques may be modified to utilize a fulcrum about which rotation and/or pivoting of one bone relative to another bone occurs via bone positioning guide 10. The fulcrum can establish and/or maintain space between adjacent bones being compressed between bone engagement member 40 and tip 50 of bone positioning guide 10, preventing lateral translation or base shift of the bones during rotation and pivoting.

Figure 30B:
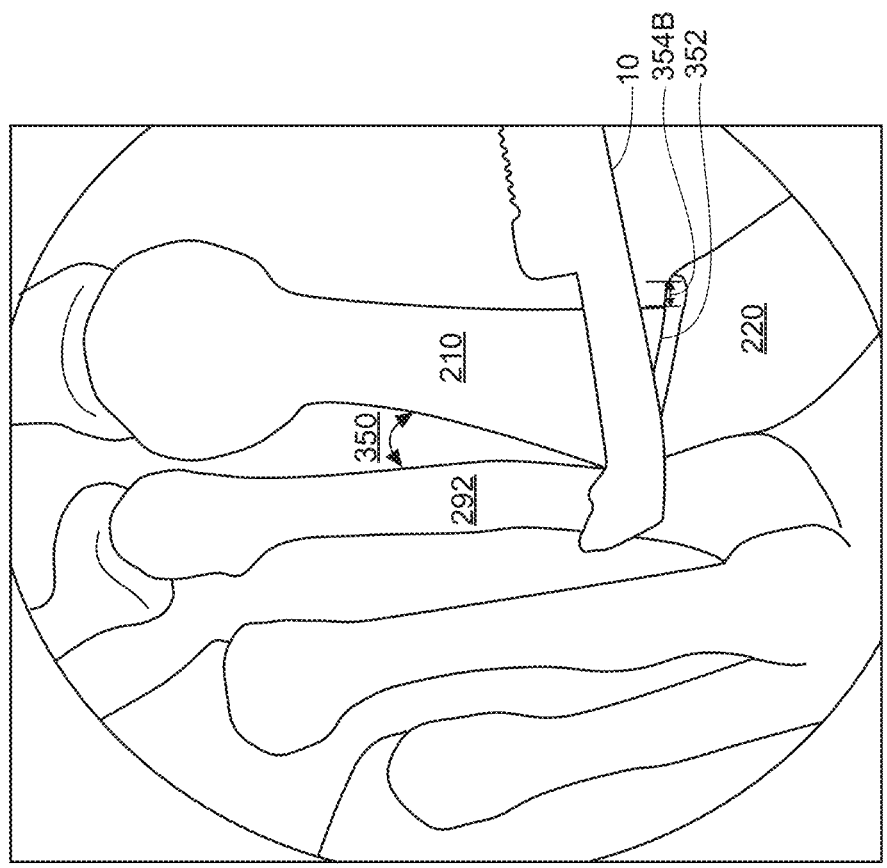
FIG. 30B shows an example base compression that can be caused after the foot of FIG. 30A is anatomically aligned.
Figure 30A:
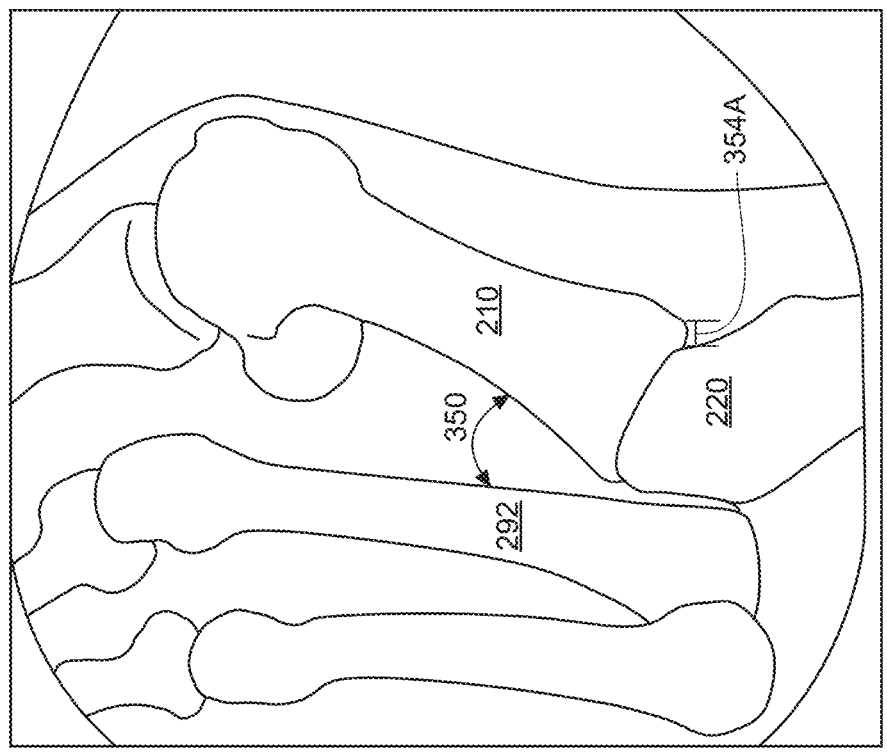
FIG. 30A illustrates a portion of a foot having a bunion caused by a misaligned first metatarsal relative to a second metatarsal.

FIG. 30A illustrates a portion of a foot having a bunion caused by a misaligned first metatarsal 210 relative to second metatarsal 292. FIG. 30B shows the foot of FIG. 30A after being anatomically aligned to correct the misalignment using bone positioning guide 10. As shown, first metatarsal 210 has been rotated counterclockwise in the frontal plane (from the perspective of a patient, clockwise from the perspective of a frontal observer) and also pivoted in the transverse plane (e.g., such that the angle 350 between the first metatarsal 210 and second metatarsal 292 is reduced). Rotation and pivoting of first metatarsal 210 can cause the base 352 of first metatarsal 210 to shift relative to medial cuneiform 220. In general, it is desirable that the offset 354A between first metatarsal 210 and medial cuneiform 220 be reduced to zero (e.g., such that there is substantially no offset) after rotation and pivoting. As shown in the illustrated application of FIG. 30B, however, the base 352 of first metatarsal 210 abutting medial cuneiform 220 has shifted toward second metatarsal 292. This results in a transverse offset 354B of first metatarsal 210 toward second metatarsal 292, causing base compression between first metatarsal 210 and second metatarsal 292.

To help avoid the base shift and offset 354B observed in FIG. 30B, a clinician can insert a fulcrum in the notch between first metatarsal 210 and second metatarsal 292 at the base of the metatarsals (e.g., adjacent respective cuneiform) before actuating bone positioning guide 10. The fulcrum can provide a point about which first metatarsal 210 can rotate and/or pivot while helping minimize or avoid base compression between the first metatarsal and the second metatarsal. In addition, use of the fulcrum may cause first metatarsal 210 and medial cuneiform 220 to be better angled relative to the guide slots of bone preparation guide 150 (once installed), providing a better cut angle through the guide slots then without use of the fulcrum. This can help reduce or eliminate unwanted spring-back, or return positioning, of first metatarsal 210 after removing bone positioning guide 10.

FIG. 31 illustrates a bone positioning operation in which a fulcrum 356 is positioned at an intersection between a first bone and a second bone, where the first bone is being realigned relative to the second bone. In particular, FIG. 31 illustrates fulcrum 356 being positioned between first metatarsal 210 and second metatarsal 292. Fulcrum 356 may be positioned distally of bone preparation guide 150 between first metatarsal 210 and second metatarsal 292 as shown in FIG. 31 or, in other applications, proximally of the guide (e.g., at the ends of the first and second metatarsals abutting the medial and intermediate cuneiform bones, respectively).

When used, the clinician can insert fulcrum 356 between first metatarsal 210 and second metatarsal 292 (or other adjacent bones, when not performing a metatarsal realignment) at any time prior to actuating bone positioning guide 10. In different embodiments, fulcrum 356 can be inserted between first metatarsal 210 and second metatarsal 292 before or after inserting joint spacer 188 and/or placing bone preparation guide 150 over the joint being operated upon. In one embodiment, the clinician prepares the joint being operated upon to release soft tissues and/or excise the plantar flare from the base of the first metatarsal 210, as discussed above. Either before or after installing bone positioning guide 10 over adjacent bones, for example with bone engagement member 40 positioned in contact with the medial ridge of the first metatarsal 210 and tip 50 positioned in contact with second metatarsal 292, the clinician inserts fulcrum 356 at the joint between the first metatarsal and the second metatarsal. The clinician can subsequently actuate bone positioning guide 10 (e.g., rotate knob 120). In the case of a left foot as shown in FIG. 31, actuation of bone positioning guide 10 causes the first metatarsal 210 to rotate counterclockwise in the frontal plane (from the perspective of a patient) and also pivot in the transverse plane about the fulcrum. In the case of a right foot (not shown), actuation causes the first metatarsal to rotate clockwise in the frontal plane (from the perspective of a patient) and also pivot in the transverse plane about the fulcrum. Thus, for both feet, actuation of bone positioning guide 10 can supinate the first metatarsal in the frontal plane and pivot the first metatarsal in the transverse plane about fulcrum 356. While use of fulcrum 356 can minimize or eliminate base compression between adjacent bones being operated upon, in other embodiments as discussed above, the described systems and techniques can be implemented without using the fulcrum.

Figure 32:
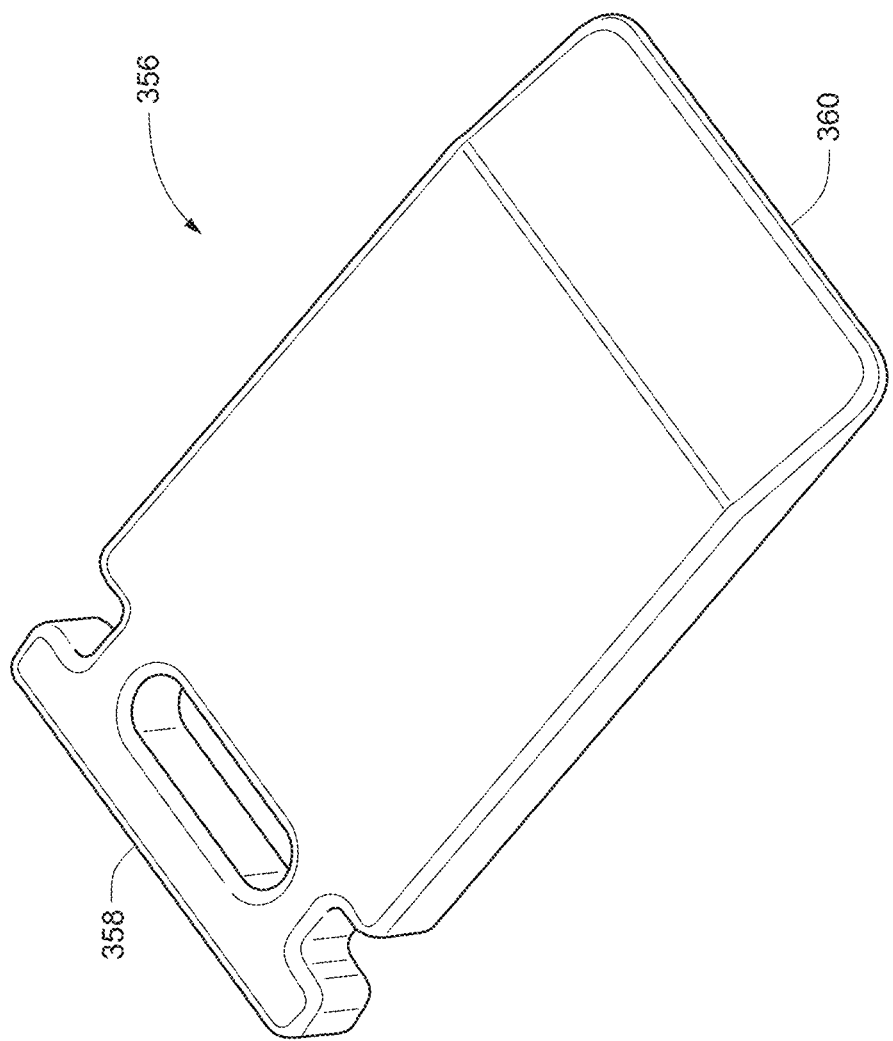
FIG. 32 is a perspective view of one example fulcrum.
Figure 33:
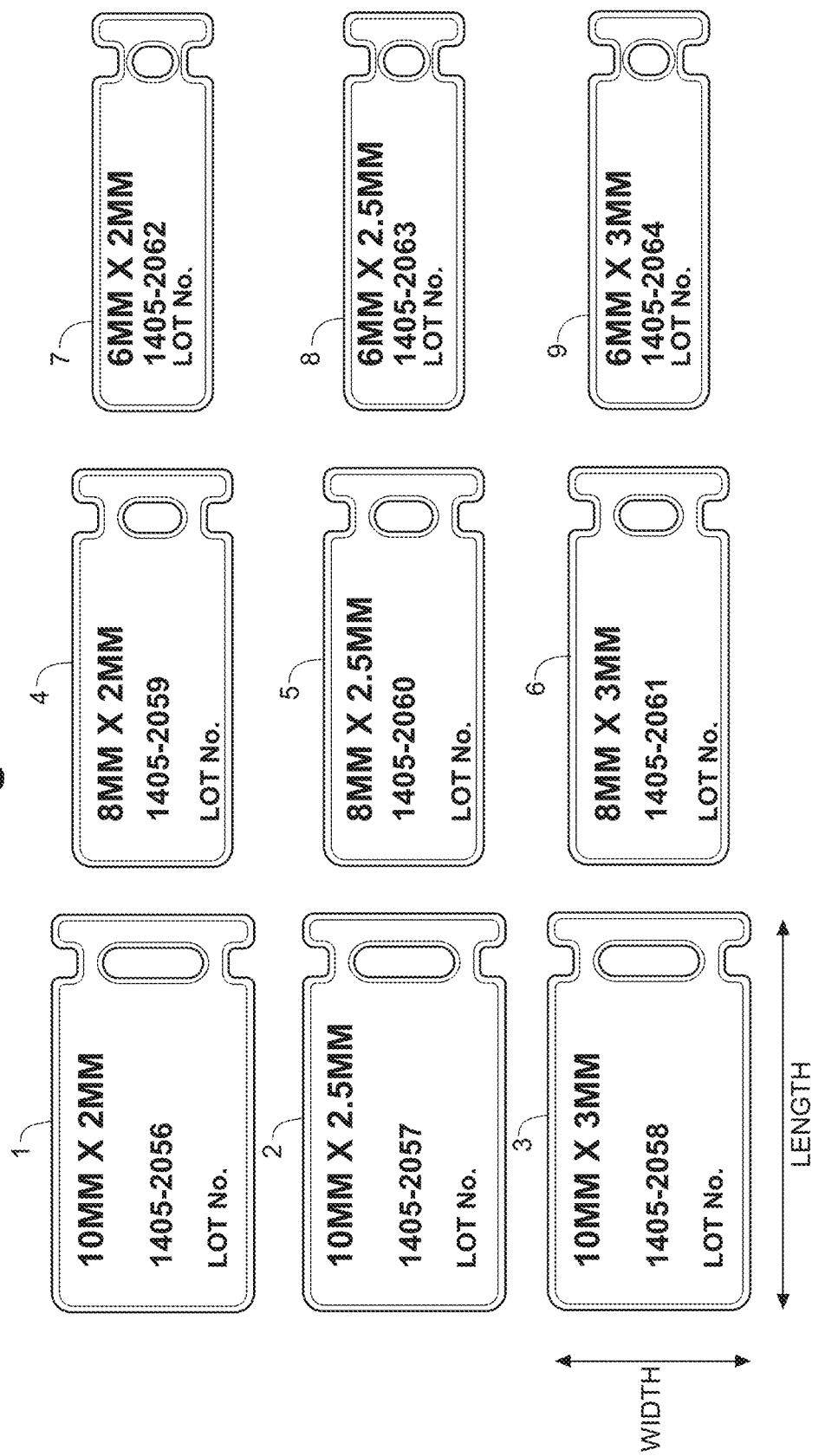
FIG. 33 illustrates an example system of different sized fulcrums.

In instances in which fulcrum 356 is used, any suitable mechanical instrument can be used for the fulcrum. FIG. 32 is a perspective view of one example instrument that can be used as fulcrum 356. In this embodiment, fulcrum 356 has a generally rectangular shape and tapers in thickness along at least a portion of the length from the trailing end 358 to the leading end 360. Fulcrum 356 may be sized sufficiently small so that it does not interfere with placement of bone preparation guide 150 on the joint being worked upon. In some embodiments, the clinician is provided a system containing multiple different size fulcrums and allowed to choose the specific sized fulcrum desired for the specific procedure being performed. FIG. 33 illustrates an example kit or system of different sized fulcrums, labeled with exemplary "width×thickness" sizes, that may be provided to a clinician in such an embodiment. In some examples, fulcrum 356 has a width ranging from 5 millimeters to 15 millimeters (e.g., about 6 millimeters to about 10 millimeters) and a thickness ranging 1 millimeter to 12 millimeters (e.g., about 2 millimeters to about 3 millimeters), although fulcrums with different dimensions can be used. While FIGS. 32 and 33 illustrate one example style of fulcrum, other mechanical instruments providing a fulcrum functionality can be used without departing from the scope of the disclosure. For instance, as alternative examples, a surgical pin or screw driver head may be used as fulcrum 356.

As discussed above, bone positioning guide 10 can have a variety of different configurations, including a configuration in which bone engagement member 40 is laterally offset from tip 50. FIG. 34 is a perspective view of bone positioning guide 10 showing an example arrangement in which bone engagement member 40 is laterally offset from tip 50. In this embodiment, the first end 60 of main body member 20 is laterally offset from an axis 362 extending through shaft 30 and a geometric center of bone engagement member 40. In particular, in the illustrated configuration, tip 50 is offset laterally in the direction of the cuneiform relative to bone engagement member 40. As a result, when bone positioning guide 10 is actuated, e.g., by rotating knob 120, a moment can be created by the offset tip. This can cause the end of the first metatarsal 210 adjacent the proximal phalange to pivot toward the second metatarsal 292 and close angle 350, e.g., while the opposite end of the first metatarsal adjacent the medial cuneiform pivots away from the second metatarsal. This can also help avoid base compression between the first and second metatarsals.

As discussed above with respect to FIGS. 19 and 20, a joint spacer 188 can be positioned in a joint between a first metatarsal and a medial cuneiform before placing bone preparation guide 150 over the joint spacer. Bone preparation guide 150 can have an opening 170 (FIG. 5) sized to receive joint spacer 188. In some examples, opening 170 of bone preparation guide 150 is size and/or shaped indexed to joint spacer 188 such that there is substantially no, or no, relative movement between the guide and spacer (once bone preparation guide 150 is placed over joint spacer 188). This can arrangement can ensure that bone preparation guide 150 is positioned precisely at the location where guided by joint spacer 188.

In practice, once bone positioning guide 150 is placed over joint spacer 188, the guide slots of the bone positioning guide may not be perfectly aligned with the ends of the bones (e.g., first metatarsal 210 and medial cuneiform 220) to be cut through the guide slots. Accordingly, in other configurations, opening 170 of bone preparation guide 150 may not be sized and/or shaped and/or indexed to joint spacer 188. In other words, opening 170 of bone positioning guide 150 may have a different cross-sectional size and/or shape than the cross-sectional size and/or shape of joint spacer 188. In these configurations, bone preparation guide 150 may actuate or rotate about an axis extending through the length of joint spacer 188. As a result, after the clinician places bone preparation guide 150 over joint spacer 188, the clinician may rotate bone preparation guide 150 around joint spacer 188 until the guide slots of the bone preparation guide are better aligned with the ends of the bones to be cut (e.g., first metatarsal 210 and medial cuneiform 220). Depending on the configuration of opening 170 of bone preparation guide 150 and the configuration of joint spacer 188, the guide may rotate freely (e.g., 360 degrees) around the joint seeker or within a bounded angular range (e.g., from plus 20 degrees to minus 20 degrees from a normal position).

Figure 35:
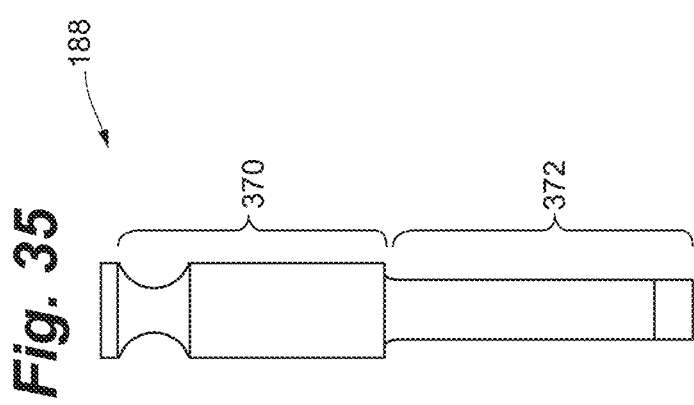
FIG. 35 illustrates an example configuration of a joint spacer that can allow a bone preparation guide to rotate around the spacer.

FIG. 35 illustrates one example configuration of a joint spacer 188 that can allow bone preparation guide 150 to rotate around the seeker. As shown in the illustrated example, joint spacer 188 has a proximal portion 370 having a cylindrical cross-section and a distal portion 372 having a rectangular cross-section. A leading edge of the distal portion 372 is insertable into the joint between the first metatarsal 210 and the medial cuneiform 220. Once bone preparation guide 150 is inserted over joint spacer 188, body 154 of the guide (FIG. 5) may be positioned about the proximal portion 370. This can allow the guide to be rotated around the proximal portion.

Figure 36B:
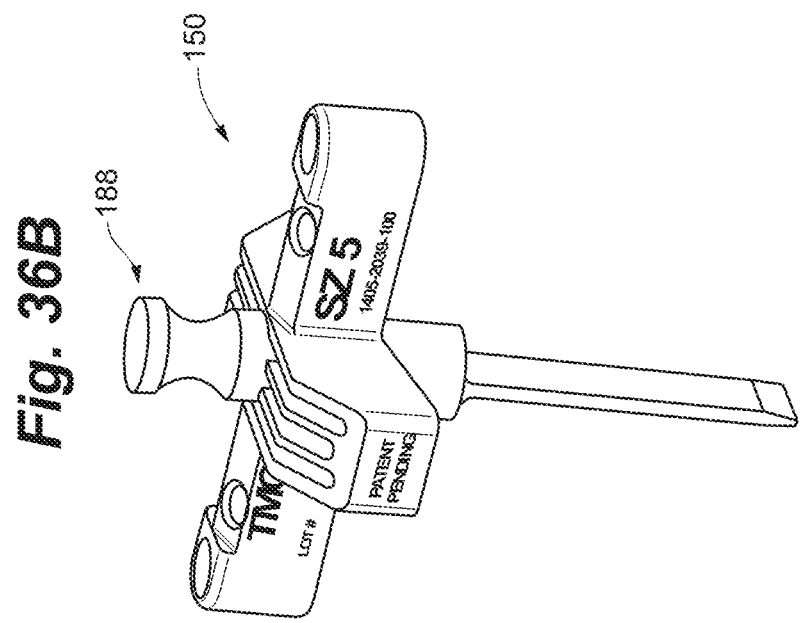
FIG. 36B is a perspective view of the example bone positioning guide of FIG. 36A shown with the joint spacer from FIG. 35 inserted into the guide.
Figure 36A:
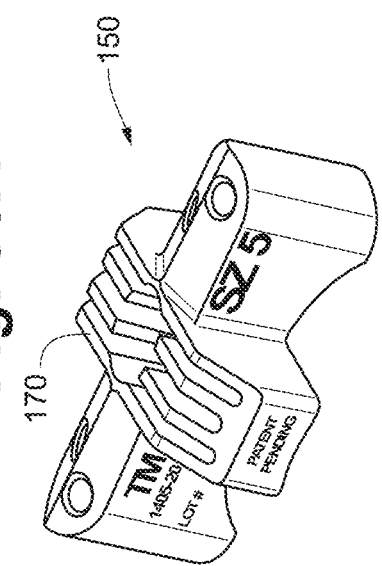
FIG. 36A is a perspective view of an example configuration of a bone positioning guide having an opening with circular cross-sectional shape.

In other configurations, opening 170 of bone positioning guide 150 may be size and/or shape indexed to the cross-sectional size and/or shape of joint spacer 188 but still provide relative rotation between the two components. For example, opening 170 may have a circular cross-section sized and shaped to receive proximal portion 370 of joint spacer 188 from FIG. 35. Because both opening 170 of bone positioning guide 150 and proximal portion 370 of joint spacer 188 have circular cross-sections in such an embodiment, the two components may rotate relative to each other. FIG. 36A is a perspective view of an example configuration of bone positioning guide 150 having an opening 170 with circular cross-sectional shape. FIG. 36B is a perspective view of the example bone positioning guide of FIG. 36A shown with joint spacer 188 from FIG. 35 inserted into the guide.

In embodiments where bone positioning guide 150 can rotate relative to joint spacer 188, the bone positioning guide and/or joint spacer may include a locking mechanism that is engageable to lock the rotational angle of the bone positioning guide relative to the joint spacer. For example, bone positioning guide 150 may include a set screw with thumb wheel that can be rotated, causing a distal end of the set screw to bear against or retract away from joint spacer 188. In use, a clinician can rotate bone preparation guide 150 around joint spacer 188 until the guide slots of the bone preparation guide are best aligned with the ends of the bones to be cut (e.g., first metatarsal 210 and medial cuneiform 220). The clinician can then engage the locking mechanism to prevent further rotation of bone preparation guide 150 relative to joint spacer 188 before performing further steps of the procedure.

Embodiments of the invention also include a disposable, sterile kit that includes an embodiment of a bone positioning guide and/or preparation guide described herein. Other components that may be included within the sterile kit include bone fixation devices.

Thus, embodiments of the invention are disclosed. Although the present invention has been described with reference to certain disclosed embodiments, the disclosed embodiments are presented for purposes of illustration, and not limitation, and other embodiments of the invention are possible. One skilled in the art will appreciate that various changes, adaptations, and modifications may be made without departing from the spirit of the invention.

The invention claimed is:

1. A method of correcting a bunion deformity, comprising the steps of:
    moving a first metatarsal from an anatomically misaligned position with respect to a second metatarsal to an anatomically aligned position with respect to the second metatarsal by applying a force to the first metatarsal, the force moving the first metatarsal to correct an alignment in more than one plane; and
    after moving the first metatarsal into the anatomically aligned position, preparing an end of the first metatarsal and preparing an opposing end of a medial cuneiform for fusion.

2. The method of claim 1, wherein the more than one plane includes any two or more of the frontal plane, transverse plane, and sagittal plane.

3. The method of claim 1, wherein the first metatarsal is rotated in the frontal plane.

4. The method of claim 1, wherein, prior to moving the first metatarsal, further including the step of mobilizing a tarsal-metatarsal joint site by releasing soft tissue or obstructing bone.

5. The method of claim 1, wherein the force is applied by a bone engagement member of a bone positioning device.

6. The method of claim 1, wherein the preparing step includes placing a tissue removing instrument in apposition to a first guide surface of a guide.

7. The method of claim 1, further including the step of placing the prepared end of the medial cuneiform in apposition with the prepared end of the first metatarsal.

8. The method of claim 6, further including the step of fixing the position of the medial cuneiform with respect to the first metatarsal by applying at least one bone fixation device across or through a joint between the apposed prepared ends of the medial cuneiform and the first metatarsal.

9. A method of correcting a bunion deformity, comprising the steps of:
    mobilizing a tarsal-metatarsal joint site by releasing soft tissue or obstructing bone;
    moving, with a bone positioning guide having a bone engagement member engaged with a first metatarsal and a tip contacting a metatarsal other than the first metatarsal, the first metatarsal from an anatomically misaligned position with respect to a second metatarsal to an anatomically aligned position with respect to the second metatarsal by applying a force to the first metatarsal, the force moving the first metatarsal to correct an alignment in more than one plane, including about an axis in a frontal plane;
    preparing an end of the first metatarsal for fusion;
    preparing an opposing end of a medial cuneiform for fusion;
    provisionally fixating a joint between the apposed prepared ends of the medial cuneiform and the first metatarsal; and
    fixing the position of the medial cuneiform with respect to the first metatarsal by applying at least one bone fixation device across or through the joint between the apposed prepared ends of the medial cuneiform and the first metatarsal.

10. The method of claim 9, wherein the end of the first metatarsal is prepared before the first metatarsal is moved into the anatomically aligned position and the end of the medial cuneiform is prepared after the first metatarsal is moved into the anatomically aligned position.

11. The method of claim 9, wherein the end of the first metatarsal is prepared after the first metatarsal is moved into the anatomically aligned position and the end of the medial cuneiform is prepared after the first metatarsal is moved into the anatomically aligned position.

12. The method of claim 9, wherein the end of the first metatarsal is prepared before the first metatarsal is moved into the anatomically aligned position and the end of the medial cuneiform is prepared before the first metatarsal is moved into the anatomically aligned position.

13. The method of claim 9, wherein the end of the first metatarsal is prepared after the first metatarsal is moved into the anatomically aligned position and the end of the medial cuneiform is prepared before the first metatarsal is moved into the anatomically aligned position.

14. The method of claim 9, further comprising, prior to moving the first metatarsal, inserting a fulcrum between the first metatarsal and the second metatarsal, wherein moving the first metatarsal from the anatomically misaligned position to the anatomically aligned position comprises rotating the first metatarsal in the frontal plane and pivoting the first metatarsal in a transverse plane about the fulcrum.

* * * * *